(12) United States Patent
Wardle et al.

(10) Patent No.: US 8,657,776 B2
(45) Date of Patent: Feb. 25, 2014

(54) OCULAR IMPLANTS FOR DELIVERY INTO THE EYE

(75) Inventors: John Wardle, San Clemente, CA (US); Andrew T. Schieber, Irvine, CA (US); Kenneth M. Galt, Laguna Hills, CA (US)

(73) Assignee: Ivantis, Inc., Irvine, CA (US)

( * ) Notice: Subject to any disclaimer, the term of this patent is extended or adjusted under 35 U.S.C. 154(b) by 0 days.

(21) Appl. No.: 13/160,355

(22) Filed: Jun. 14, 2011

(65) Prior Publication Data

US 2012/0323159 A1 Dec. 20, 2012

(51) Int. Cl.
*A61F 9/00* (2006.01)
(52) U.S. Cl.
USPC .......... 604/8; 604/9; 606/107; 606/108; 623/4.1
(58) Field of Classification Search
CPC ............... A61F 9/00; A61F 9/00781
USPC .......... 604/8, 9, 107, 108; 606/107, 108; 623/4.1
See application file for complete search history.

(56) References Cited

U.S. PATENT DOCUMENTS

| | | |
|---|---|---|
| 3,788,327 A | 1/1974 | Donowitz et al. |
| 3,948,271 A | 4/1976 | Akiyama |
| 4,037,604 A | 7/1977 | Newkirk |
| 4,428,746 A | 1/1984 | Mendez |
| 4,457,757 A | 7/1984 | Molteno |
| 4,722,724 A | 2/1988 | Schocket |
| 4,733,665 A | 3/1988 | Palmaz |
| 4,750,901 A | 6/1988 | Molteno |
| 4,826,478 A | 5/1989 | Schocket |
| 4,886,488 A | 12/1989 | White |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |

(Continued)

FOREIGN PATENT DOCUMENTS

| | | |
|---|---|---|
| AU | 1998/76197 B2 | 2/1999 |
| CN | 1950091 A | 4/2007 |

(Continued)

OTHER PUBLICATIONS

Wardle, John; U.S. Appl. No. 13/167,644 entitled "Ocular implants deployed in schlemm's canal of the eye," filed Jun. 23, 2011.

(Continued)

*Primary Examiner* — Philip R Wiest
*Assistant Examiner* — Ariana Zimbouski
(74) *Attorney, Agent, or Firm* — Shay Glenn LLP

(57) ABSTRACT

An ocular implant adapted to reside at least partially in a portion of Schlemm's canal of an eye. The implant includes a spine extending along a longitudinal axis of the implant, a plurality of curved supports extending from the spine, each support comprising a first end extending from a first location on a first side of the spine and a second end extending from a second location on a second side of the spine, the second location being proximal to the first location, so that each support forms a portion of a helix, the spine and supports defining a volume having a maximum width perpendicular to the longitudinal axis between 0.005 inches and 0.04 inches, the ocular implant being configured to bend preferentially in a preferential bending plane.

14 Claims, 22 Drawing Sheets

(56) References Cited

U.S. PATENT DOCUMENTS

| | | | |
|---|---|---|---|
| 5,092,837 A | 3/1992 | Ritch et al. |
| 5,127,901 A | 7/1992 | Odrich |
| 5,178,604 A | 1/1993 | Baerveldt et al. |
| 5,180,362 A | 1/1993 | Worst |
| 5,213,569 A | 5/1993 | Davis |
| 5,246,452 A | 9/1993 | Sinnott |
| 5,360,399 A | 11/1994 | Stegmann |
| 5,372,577 A | 12/1994 | Ungerleider |
| 5,454,796 A | 10/1995 | Krupin |
| 5,458,615 A | 10/1995 | Klemm et al. |
| 5,591,223 A | 1/1997 | Lock et al. |
| 5,626,558 A | 5/1997 | Suson |
| 5,792,099 A | 8/1998 | DeCamp et al. |
| 5,807,302 A | 9/1998 | Wandel |
| 5,865,831 A | 2/1999 | Cozean et al. |
| 5,868,697 A | 2/1999 | Richter et al. |
| 5,879,319 A | 3/1999 | Pynson et al. |
| 5,893,837 A | 4/1999 | Eagles et al. |
| 5,948,427 A | 9/1999 | Yamamoto et al. |
| 5,968,058 A | 10/1999 | Richter et al. |
| 6,007,511 A | 12/1999 | Prywes |
| 6,050,970 A | 4/2000 | Baerveldt |
| 6,102,045 A | 8/2000 | Nordquist et al. |
| 6,186,974 B1 | 2/2001 | Allan et al. |
| 6,221,078 B1 | 4/2001 | Bylsma |
| 6,238,409 B1 | 5/2001 | Hojeibane |
| D444,874 S | 7/2001 | Haffner et al. |
| 6,375,642 B1 | 4/2002 | Grieshaber et al. |
| 6,409,752 B1* | 6/2002 | Boatman et al. ............ 623/1.15 |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2* | 12/2004 | Lynch et al. ................... 604/8 |
| 6,827,700 B2 | 12/2004 | Lynch et al. |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,094,225 B2 | 8/2006 | Tu et al. |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,034,105 B2 | 10/2011 | Stegmann et al. |
| 8,123,729 B2 | 2/2012 | Yamamoto et al. |
| 8,308,701 B2 | 11/2012 | Horvath et al. |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2003/0004457 A1 | 1/2003 | Andersson |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0093084 A1 | 5/2003 | Nissan et al. |
| 2003/0097151 A1 | 5/2003 | Smedley et al. |
| 2003/0181848 A1 | 9/2003 | Bergheim et al. |
| 2003/0187384 A1 | 10/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0082939 A1 | 4/2004 | Berlin |
| 2004/0088048 A1 | 5/2004 | Richter et al. |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0249333 A1 | 12/2004 | Bergheim et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0244464 A1 | 11/2005 | Hughes |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0149194 A1 | 7/2006 | Conston et al. |
| 2006/0154981 A1 | 7/2006 | Klimko et al. |
| 2006/0155238 A1 | 7/2006 | Shields |

(56) References Cited

U.S. PATENT DOCUMENTS

| | | |
|---|---|---|
| 2006/0155300 A1 | 7/2006 | Stamper et al. |
| 2006/0173397 A1 | 8/2006 | Tu et al. |
| 2006/0178674 A1 | 8/2006 | McIntyre |
| 2006/0189915 A1 | 8/2006 | Camras et al. |
| 2006/0189916 A1 | 8/2006 | Bas et al. |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0241749 A1 | 10/2006 | Tu et al. |
| 2007/0010827 A1 | 1/2007 | Tu et al. |
| 2007/0073275 A1 | 3/2007 | Conston et al. |
| 2007/0088432 A1 | 4/2007 | Solovay et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0179520 A1 | 8/2007 | West |
| 2007/0191863 A1* | 8/2007 | De Juan et al. ............... 606/108 |
| 2007/0202186 A1 | 8/2007 | Yamamoto et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0298068 A1 | 12/2007 | Badawi et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0228127 A1 | 9/2008 | Burns et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0043321 A1 | 2/2009 | Conston et al. |
| 2009/0069786 A1 | 3/2009 | Vesely et al. |
| 2009/0082860 A1* | 3/2009 | Schieber et al. ............... 623/4.1 |
| 2009/0082862 A1 | 3/2009 | Schieber et al. |
| 2009/0104248 A1 | 4/2009 | Rapacki et al. |
| 2009/0132040 A1 | 5/2009 | Frion et al. |
| 2009/0138081 A1 | 5/2009 | Bergheim et al. |
| 2009/0182421 A1 | 7/2009 | Silvestrini et al. |
| 2009/0227934 A1* | 9/2009 | Euteneuer et al. ............... 604/8 |
| 2009/0247955 A1 | 10/2009 | Yamamoto et al. |
| 2009/0281520 A1 | 11/2009 | Highley et al. |
| 2010/0004580 A1 | 1/2010 | Lynch et al. |
| 2010/0057072 A1* | 3/2010 | Roman et al. ................... 606/33 |
| 2010/0121342 A1 | 5/2010 | Schieber et al. |
| 2010/0137981 A1 | 6/2010 | Silvestrini et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0222733 A1 | 9/2010 | Schieber et al. |
| 2010/0234726 A1 | 9/2010 | Sirimanne et al. |
| 2010/0234790 A1 | 9/2010 | Tu et al. |
| 2011/0009874 A1 | 1/2011 | Wardle et al. |
| 2011/0009958 A1 | 1/2011 | Wardle et al. |
| 2011/0098809 A1 | 4/2011 | Wardle et al. |
| 2011/0196487 A1 | 8/2011 | Badawi et al. |
| 2011/0218523 A1 | 9/2011 | Robl |
| 2012/0010702 A1 | 1/2012 | Stegmann et al. |
| 2012/0022424 A1 | 1/2012 | Yamamoto et al. |
| 2012/0035524 A1 | 2/2012 | Silvestrini |
| 2012/0136439 A1 | 5/2012 | Schieber et al. |
| 2012/0191064 A1 | 7/2012 | Conston et al. |
| 2012/0271272 A1 | 10/2012 | Hammack et al. |
| 2013/0006165 A1 | 1/2013 | Euteneuer et al. |
| 2013/0079701 A1 | 3/2013 | Schieber et al. |
| 2013/0267887 A1 | 10/2013 | Kahook et al. |

FOREIGN PATENT DOCUMENTS

| | | |
|---|---|---|
| DE | 4226476 C1 | 8/1993 |
| DE | 19840047 A1 | 3/2000 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| JP | H10-504978 A | 5/1998 |
| JP | 11123205 | 5/1999 |
| JP | 2006289075 A | 10/2006 |
| WO | WO 00/07525 A1 | 2/2000 |
| WO | WO 00/64389 A1 | 11/2000 |
| WO | WO 00/64393 A1 | 11/2000 |
| WO | WO 01/97727 A1 | 12/2001 |
| WO | WO 02/36052 A1 | 5/2002 |
| WO | WO 02/074052 A2 | 9/2002 |
| WO | WO 02/080811 A2 | 10/2002 |
| WO | WO 03/015659 A2 | 2/2003 |
| WO | WO 03/045290 A1 | 6/2003 |
| WO | WO 2004/054643 A1 | 7/2004 |
| WO | WO 2004/093761 A1 | 11/2004 |
| WO | WO 2005/105197 A2 | 11/2005 |
| WO | WO 2006/066103 A2 | 6/2006 |
| WO | WO 2007/035356 A2 | 3/2007 |
| WO | WO 2007/047744 A2 | 4/2007 |
| WO | WO 2007/087061 A2 | 8/2007 |
| WO | WO2008/002377 A1 | 1/2008 |
| WO | WO 2008/005873 A2 | 1/2008 |
| WO | WO 2009/120960 A2 | 10/2009 |
| WO | WO 2011/053512 A1 | 5/2011 |
| WO | WO 2011/057283 A1 | 5/2011 |
| WO | WO 2011/106781 A1 | 9/2011 |
| WO | WO 2011/150045 A1 | 12/2011 |
| WO | WO 2012/051575 A2 | 4/2012 |

OTHER PUBLICATIONS

Bahler, et al.; Trabecular bypass stents decrease intraocular pressure in cultured human anterior segments; Amer. Journal of Ophthalmology; vol. 138, No. 6; pp. 988-994.e2; Dec. 2004.

D'Ermo, et al.; Our results with the operation of ab externo trabeculotomy; Ophthalmologica; vol. 163; pp. 347-355; 1971.

Ellingsen et al.; Trabeculotomy and sinusotomy in enucleated human eyes; Investigative Ophthalmology; vol. 11; pp. 21-28; Jan. 1972.

Grant; Experimental aqueous perfusion in enucleated human eyes; Archives of Ophthalmology; vol. 69; pp. 783-801; Jun. 1963.

Johnstone et al.; "Microsurgery of Schlemm's Canal and the Human Aqueous Outflow System;" American Journal of Ophthalmology, vol. 76 (6): 906-917; Dec. 1973.

Lee et al.; Aqueous-venous shunt and intraocular pressure. Preliminary report of animal studies; Investigative Ophthalmology; vol. 5; No. 1; pp. 59-64; Feb. 1966.

Moses, Robert; The effect of intraocular pressure on resistance to outflow; Survey of Ophthalmology; vol. 22; No. 2; pp. 88-100; Sep.-Oct. 1977.

Mäepea et al.; The pressures in the episcleral veins, schlemm's canal and the trabecular meshwork in monkeys: effects of changes in intraocular pressure; Exp. Eye Res.; vol. 49; pp. 645-663; 1989.

Rosenquist et al.; Outflow resistanc of enucleated human eyes at two different perfusion pressures and differenct extents of trabeculotomy; Current Eye Res.; vol. 8; No. 12; pp. 1233-1240; 1989.

Savage, James; Gonioscopy in the management of glaucoma; Am. Academy of Ophthalmology; Focal Points; vol. XXIV; No. 3; pp. 1-14; Mar. 2006.

Schultz, Jared; Canaloplasty procedure shows promise for open-angle glaucoma in European study; Ocular Surgery News; vol. 34; Mar. 1, 2007.

Smit et al.; Effects of viscoelastic injection into schlemm's canal in primate and human eyes; J. Am. Academy of Ophthalmology; vol. 109; No. 4; pp. 786-792; Apr. 20002.

Spiegel et al.; Schlemm's canal implant: a new method to lower intraocular pressure in patients with POAG?; Ophthalmic Surgery and Lasers; vol. 30; No. 6; pp. 492-494; Jun. 1999.

(56) References Cited

OTHER PUBLICATIONS

Lynch, Mary G.; U.S. Appl. No. 60/131,030 entitled "Devices and methods for treating glaucoma by enhancing aqueous outflow through schlemm's canal and anterior chamber angle ," filed Apr. 26, 1999.

Wardle et al.; U.S. Appl. No. 13/330,592 entitled "Delivering Ocular Implants Into the Eye," filed Dec. 19, 2011.

Schieber et al.; U.S. Appl. No. 13/425,874 entitled "Glaucoma Treatment Method," filed Mar. 21, 2012.

Schieber et al.; U.S. Appl. No. 13/763,394 entitled "Ocular Implant Architectures," filed Feb. 8, 2013.

Schieber et al.; U.S. Appl. No. 13/776,592 entitled "Glaucoma Treatment Method," filed Feb. 25, 2013.

Wardle et al.; U.S. Appl. No. 13/744,351 entitled "Suspended goniolens system," filed Jan. 17, 2013.

Wardle et al.; U.S. Appl. No. 13/793,638 entitled "Ocular Implants for Delivery into an Anterior Chamber of the Eye," filed Mar. 11, 2013.

* cited by examiner

OCULAR IMPLANTS FOR DELIVERY INTO THE EYE

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to devices that are implanted within the eye. More particularly, the present invention relates to systems, devices and methods for delivering ocular implants into the eye.

BACKGROUND OF THE INVENTION

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," Investigative Ophthalmology (February 1966)). Other early glaucoma treatment implants led from the anterior chamber to a subconjunctival bleb (e.g., U.S. Pat. No. 4,968,296 and U.S. Pat. No. 5,180,362). Still others were shunts leading from the anterior chamber to a point just inside Schlemm's canal (Spiegel et al., "Schlemm's canal implant: a new method to lower intraocular pressure in patients with POAG?" Ophthalmic Surgery and Lasers (June 1999); U.S. Pat. No. 6,450,984; U.S. Pat. No. 6,450,984).

SUMMARY OF THE INVENTION

One aspect of the invention provides an ocular implant adapted to reside at least partially in a portion of Schlemm's canal of an eye. The implant includes a spine extending along a longitudinal axis of the implant, a plurality of curved supports extending from the spine, each support comprising a first end extending from a first location on a first side of the spine and a second end extending from a second location on a second side of the spine, the second location being proximal to the first location, so that each support forms a portion of a helix, the spine and supports defining a volume having a maximum width perpendicular to the longitudinal axis between 0.005 inches and 0.04 inches, the ocular implant being configured to bend preferentially in a preferential bending plane.

In some embodiments, the longitudinal axis of the ocular implant is curved in the preferential bending plane. The volume defined by the ocular implant may have a circular cross-section or a non-circular cross-section. In embodiments in which the implant has a non-circular cross-section, the spine may be disposed on a longer side of the non-circular cross-section.

In some embodiments, an aspect ratio of the width of the spine to the thickness of the spine is such that the spine bends preferentially in the preferential bending plane. The aspect ratio of the width to the thickness is greater than one in some embodiments, e.g., an aspect ratio of about three.

In some embodiments, an aspect ratio of the spine's first lateral extent to the spine's second lateral extent is such that the spine bends preferentially in the preferential bending plane. The aspect ratio of the first lateral extent to the second lateral extent is greater than one in some embodiments, and may be greater than three.

In some embodiments, the supports and spine define a lumen and a plurality of openings fluidly communicating with the lumen, the ocular implant being more than 50% open due to the openings defined by the supports and spine.

In various embodiments the ocular implant is configured to reshape a trabecular meshwork of the eye when the ocular implant is placed within a portion of Schlemm's canal of the eye. The ocular implant may also be configured to reshape Schlemm's canal when the ocular implant is placed therein.

In some embodiments, the second end of a first support of the plurality of supports is at least partially proximal to the first end of a second support of the plurality of supports. The supports may form a helical element having a plurality of turns, with the spine interconnecting adjacent turns formed by the helical element. In some embodiments, the longitudinal axis has radius of curvature that varies along the length thereof.

Another aspect of the invention provides an ocular implant adapted to reside at least partially in a portion of Schlemm's canal of an eye. In some embodiments the implant has a spine extending along a longitudinal axis of the implant, a plurality of supports extending from the spine at a plurality of longitudinally spaced support locations, each support comprising a dorsal loop extending from a first side of the spine and a ventral loop extending from a second side of the spine opposite the first side, and an elongate opening extending along the longitudinal axis and bordered by the spine and the dorsal and ventral loops of the supports, the spine extending continuously through the support locations, the spine and supports defining a volume having a maximum width perpendicular to the longitudinal axis between 0.005 inches and 0.04 inches, the ocular implant being configured to bend preferentially in a preferential bending plane.

In some embodiments, the longitudinal axis of the ocular implant is curved in the preferential bending plane. The volume defined by the ocular implant may have a circular cross-section or a non-circular cross-section. In embodiments in which the implant has a non-circular cross-section, the spine may be disposed on a longer side of the non-circular cross-section.

In some embodiments, an aspect ratio of the width of the spine to the thickness of the spine is such that the spine bends preferentially in the preferential bending plane. The aspect ratio of the width to the thickness is greater than one in some embodiments, e.g., an aspect ratio of about three.

In some embodiments, an aspect ratio of the spine's first lateral extent to the spine's second lateral extent is such that the spine bends preferentially in the preferential bending plane. The aspect ratio of the first lateral extent to the second lateral extent is greater than one in some embodiments, and may be greater than three.

In some embodiments, the supports and spine define a lumen and a plurality of openings fluidly communicating with the lumen, the ocular implant being more than 50% open due to the openings defined by the supports and spine.

In various embodiments the ocular implant is configured to reshape a trabecular meshwork of the eye when the ocular implant is placed within a portion of Schlemm's canal of the eye. The ocular implant may also be configured to reshape Schlemm's canal when the ocular implant is placed therein.

In some embodiments, the second end of a first support of the plurality of supports is at least partially proximal to the first end of a second support of the plurality of supports. The supports may form a helical element having a plurality of turns, with the spine interconnecting adjacent turns formed by the helical element. In some embodiments, the longitudinal axis has radius of curvature that varies along the length thereof.

Still another aspect of the invention provides a method of deploying at least a distal portion of an ocular implant into Schlemm's canal of an eye, the eye having a cornea defining an anterior chamber and an iris defining a pupil. In some embodiments, the method includes the steps of: advancing a distal portion of a cannula through the cornea so that a curved portion of the cannula is at least partially disposed in the anterior chamber of the eye; advancing a distal tip of the cannula through trabecular meshwork of the eye so that a distal opening of the cannula is placed in fluid communication with Schlemm's canal; advancing an ocular implant through the curved portion of the cannula; and rotating the ocular implant as at least a distal portion of the ocular implant is advanced through the distal opening and into Schlemm's canal.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1:
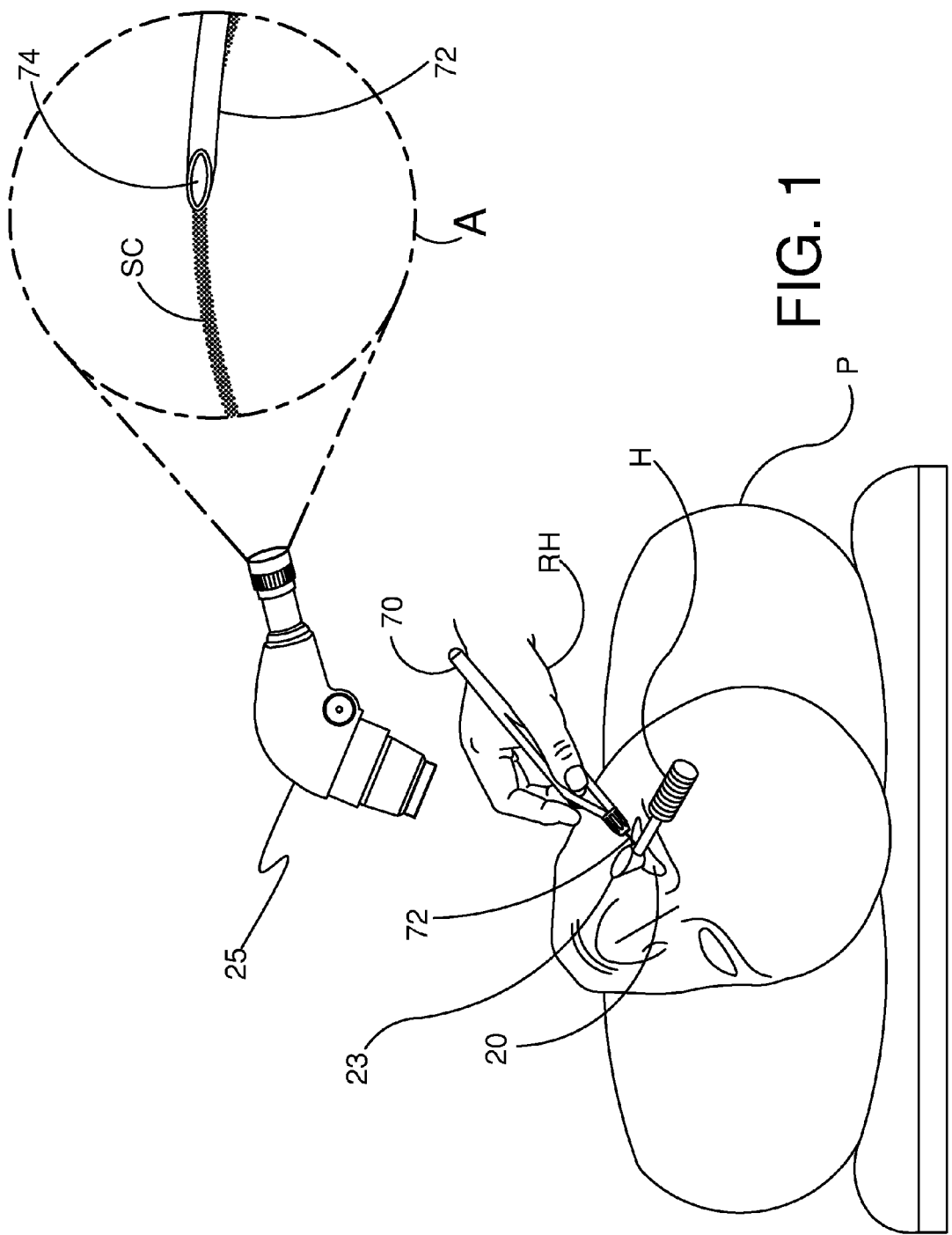
FIG. 1 is a stylized representation of an exemplary medical procedure in accordance with this detailed description.

FIG. 1 is a stylized representation of an exemplary medical procedure in accordance with this detailed description. In the exemplary procedure of FIG. 1, a physician is treating an eye 20 of a patient P. In the exemplary procedure of FIG. 1, the physician is holding a hand piece of a delivery system 70 in his or her right hand RH. The physician's left hand (not shown) may be used to hold the handle H of a gonio lens 23. It will be appreciated that some physician's may prefer holding the delivery system hand piece in the left hand and the gonio lens handle H in the right hand RH.

During the exemplary procedure illustrated in FIG. 1, the physician may view the interior of the anterior chamber using gonio lens 23 and a microscope 25. Detail A of FIG. 1 is a stylized simulation of the image viewed by the physician. A distal portion of a cannula 72 is visible in Detail A. A shadow-like line indicates the location of Schlemm's canal SC which is lying under various tissue (e.g., the trabecular meshwork) that surround the anterior chamber. A distal opening 74 of cannula 72 is positioned near Schlemm's canal SC of eye 20.

Exemplary methods in accordance with this detailed description may include the step of advancing the distal end of cannula 72 through the cornea of eye 20 so that a distal portion of cannula 72 is disposed in the anterior chamber of the eye. Cannula 72 may then be used to access Schlemm's canal of the eye, for example, by piercing the wall of Schlemm's canal with the distal end of cannula 72. Distal opening 74 of cannula 72 may be placed in fluid communication with a lumen defined by Schlemm's canal. The ocular implant may be advanced out of distal opening 74 and into Schlemm's canal. Insertion of the ocular implant into Schlemm's canal may facilitate the flow of aqueous humor out of the anterior chamber of the eye.

Figure 2:
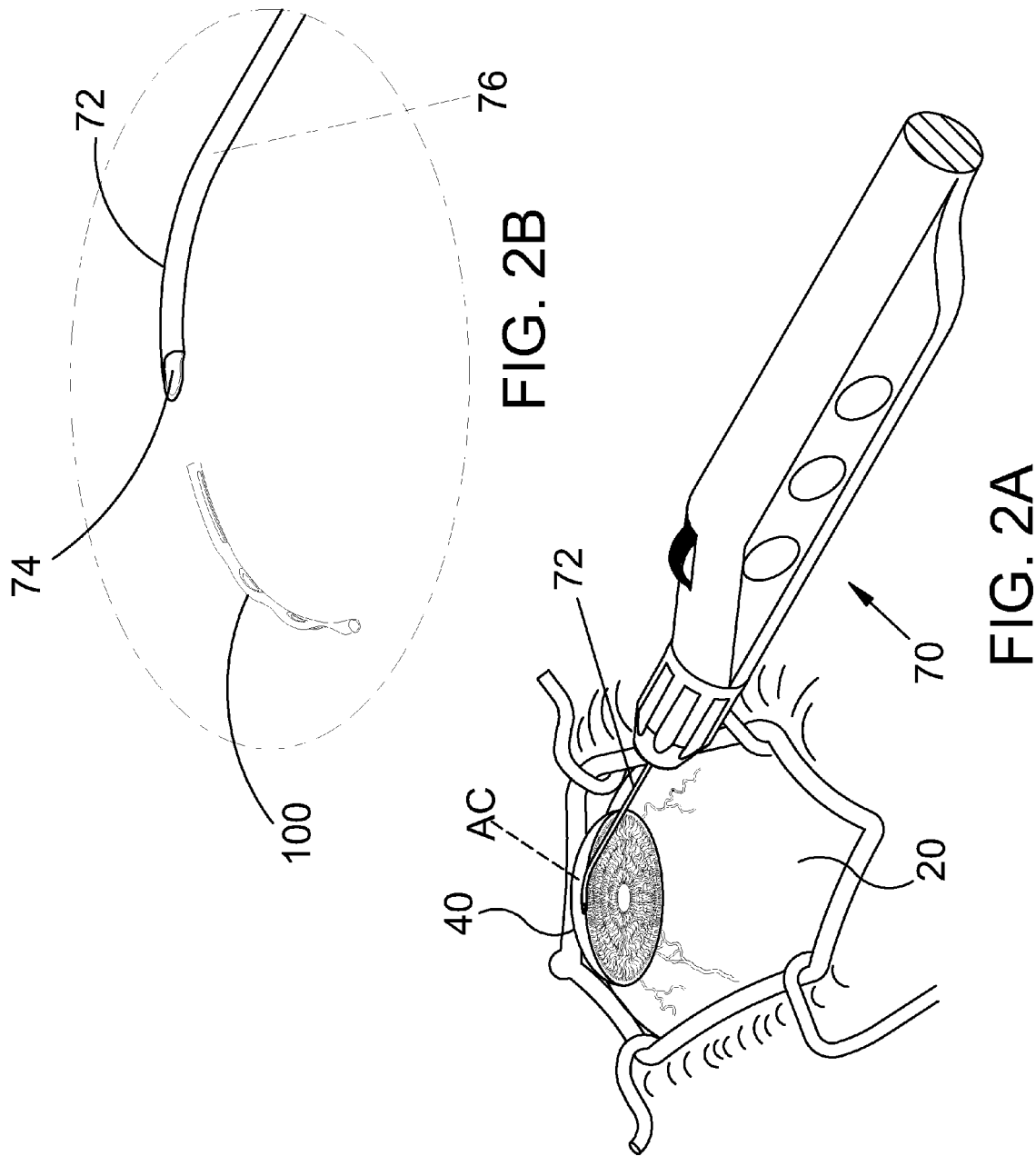
FIG. 2A is a perspective view further illustrating a delivery system used in the exemplary medical procedure shown in the previous figure.
FIG. 2B is an enlarged detail view further illustrating a cannula of the delivery system shown in the previous figure.

FIG. 2A is a perspective view further illustrating delivery system 70 and eye 20 shown in the previous figure. In FIG. 2A, cannula 72 of delivery system 70 is shown extending through a cornea 40 of eye 20. A distal portion of cannula 72 is disposed inside an anterior chamber AC defined by cornea 40 of eye 20. In the embodiment of FIG. 2A, cannula 72 is configured so that a distal opening 74 of cannula 72 can be placed in fluid communication with Schlemm's canal.

In the embodiment of FIG. 2A, an ocular implant is disposed in a passageway defined by cannula 72. Delivery system 70 includes a mechanism that is capable of advancing and retracting the ocular implant along the length of cannula 72. The ocular implant may be placed in Schlemm's canal of eye 20 by advancing the ocular implant through the distal opening of cannula 72 while the distal opening is in fluid communication with Schlemm's canal.

FIG. 2B is an enlarged detail view further illustrating cannula 72 of delivery system 70. In the illustrative embodiment of FIG. 2B, an ocular implant 100 has been advanced through distal opening 74 of cannula 72. Cannula 72 of FIG. 2B defines a passageway 76 that fluidly communicates with distal opening 74. Ocular implant 100 may be moved along passageway 76 and through distal opening 74 by delivery system 70. Delivery system 70 includes a mechanism capable of performing this function.

Figure 3:
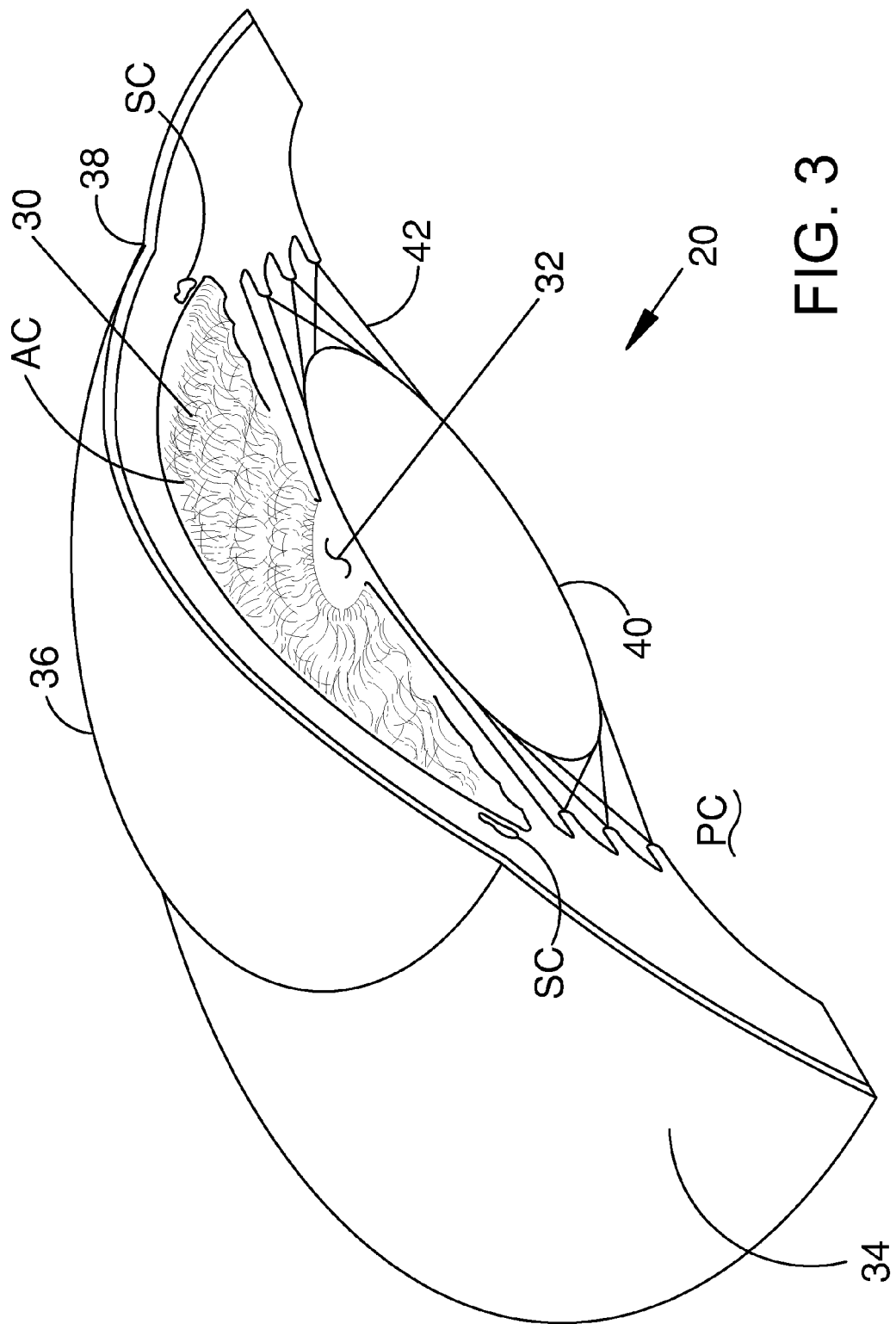
FIG. 3 is a stylized perspective view illustrating the anatomy of an eye.

FIG. 3 is a stylized perspective view illustrating a portion of eye 20 discussed above. Eye 20 includes an iris 30 defining a pupil 32. In FIG. 3, eye 20 is illustrated in a cross-sectional view created by a cutting plane passing through the center of pupil 32. Eye 20 can be conceptualized as a fluid filled ball having two chambers. Sclera 34 of eye 20 surrounds a posterior chamber PC filled with a viscous fluid known as vitreous humor. Cornea 36 of eye 20 encloses an anterior chamber AC that is filled with a fluid known as aqueous humor. The cornea 36 meets the sclera 34 at a limbus 38 of eye 20. A lens 40 of eye 20 is located between anterior chamber AC and posterior chamber PC. Lens 40 is held in place by a number of ciliary zonules 42.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

Schlemm's canal SC is a tube-like structure that encircles iris 30. Two laterally cut ends of Schlemm's canal SC are visible in the cross-sectional view of FIG. 3. In a healthy eye, aqueous humor flows out of anterior chamber AC and into Schlemm's canal SC. Aqueous humor exits Schlemm's canal SC and flows into a number of collector channels. After leaving Schlemm's canal SC, aqueous humor is absorbed into the venous blood stream and carried out of the eye.

Figure 4:
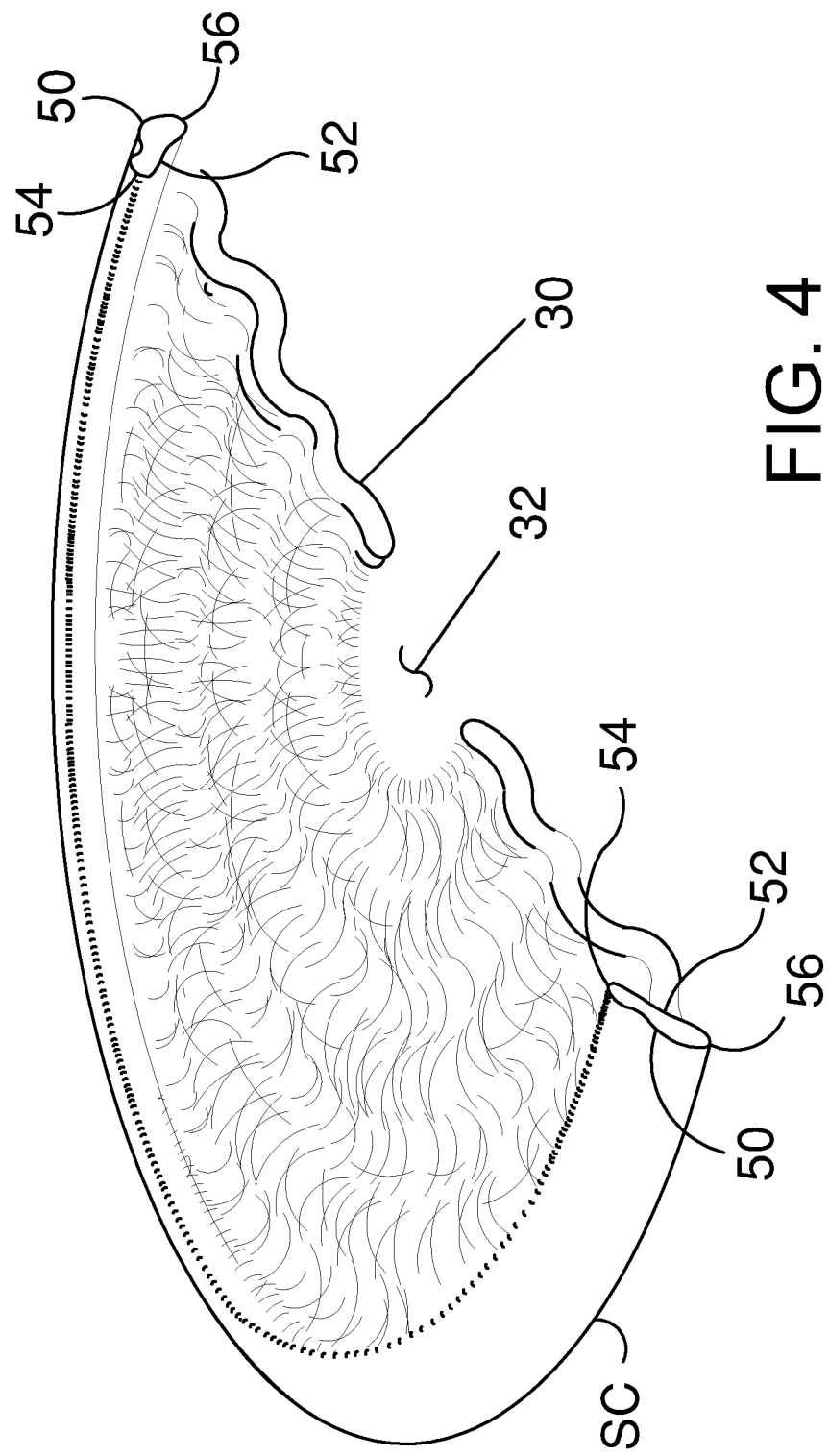
FIG. 4 is a stylized perspective view showing Schlemm's canal and an iris of the eye shown in the previous figure.

FIG. 4 is a stylized perspective view showing Schlemm's canal SC and iris 30 of eye 20 shown in the previous figure. In FIG. 4, Schlemm's canal SC is shown encircling iris 30. With reference to FIG. 4, it will be appreciated that Schlemm's canal SC may overhang iris 30 slightly. Iris 30 defines a pupil 32. In the exemplary embodiment of FIG. 4, Schlemm's canal SC and iris 30 are shown in cross-section, with a cutting plane passing through the center of pupil 32.

The shape of Schlemm's canal SC is somewhat irregular, and can vary from patient to patient. The shape of Schlemm's canal SC may be conceptualized as a cylindrical-tube that has been partially flattened. With reference to FIG. 4, it will be appreciated that Schlemm's canal SC has a first major side 50, a second major side 52, a first minor side 54, and a second minor side 56.

Schlemm's canal SC forms a ring around iris 30 with pupil 32 disposed in the center of that ring. With reference to FIG. 4, it will be appreciated that first major side 50 is on the outside of the ring formed by Schlemm's canal SC and second major side 52 is on the inside of the ring formed by Schlemm's canal SC. Accordingly, first major side 50 may be referred to as an outer major side of Schlemm's canal SC and second major side 52 may be referred to as an inner major side of Schlemm's canal SC. With reference to FIG. 4, it will be appreciated that first major side 50 is further from pupil 32 than second major side 52. The outer major wall of Schlemm's canal is supported by scleral tissue of the eye. Elevated pressure inside the eye of a patient suffering from glaucoma may cause the inside major wall of Schlemm's canal to be pressed against the outer major wall of the canal.

Figure 5:
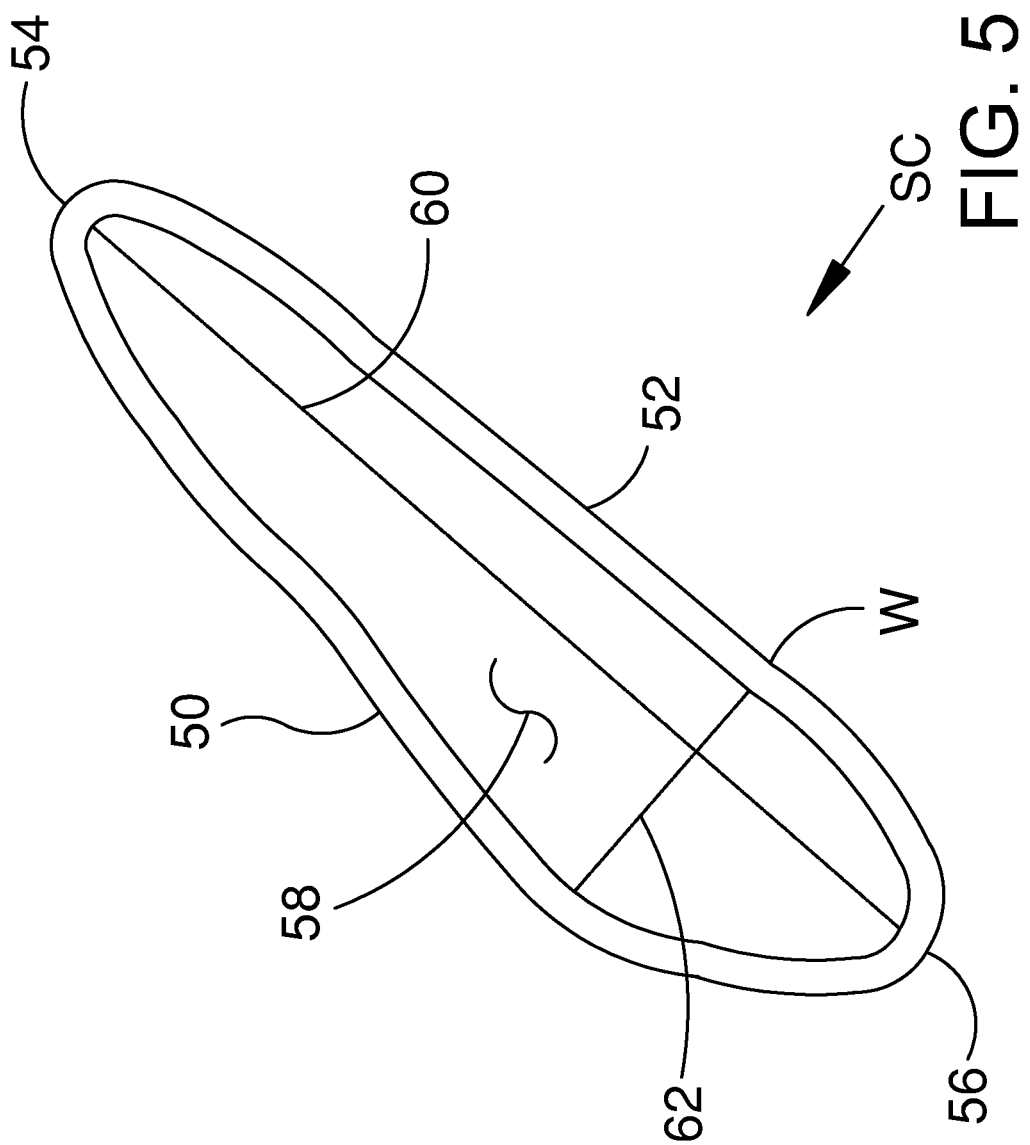
FIG. 5 is an enlarged cross-sectional view further illustrating Schlemm's canal SC shown in the previous figure.

FIG. 5 is an enlarged cross-sectional view further illustrating Schlemm's canal SC shown in the previous figure. With reference to FIG. 5, it will be appreciated that Schlemm's canal SC comprises a wall W defining a lumen 58. The shape of Schlemm's canal SC is somewhat irregular, and can vary from patient to patient. The shape of Schlemm's canal SC may be conceptualized as a cylindrical-tube that has been partially flattened. The cross-sectional shape of lumen 58 may be compared to the shape of an ellipse. A major axis 60 and a minor axis 62 of lumen 58 are illustrated with dashed lines in FIG. 5.

The length of major axis 60 and minor axis 62 can vary from patient to patient. The length of minor axis 62 is between one and thirty micrometers in most patients. The length of major axis 60 is between one hundred and fifty micrometers and three hundred and fifty micrometers in most patients.

With reference to FIG. 5, it will be appreciated that Schlemm's canal SC comprises a first major side 50, a second major side 52, a first minor side 54, and a second minor side 56. In the exemplary embodiment of FIG. 5, first major side 50 is longer than both first minor side 54 and second minor side 56. Also in the exemplary embodiment of FIG. 5, second major side 52 is longer than both first minor side 54 and second minor side 56.

Figure 6:
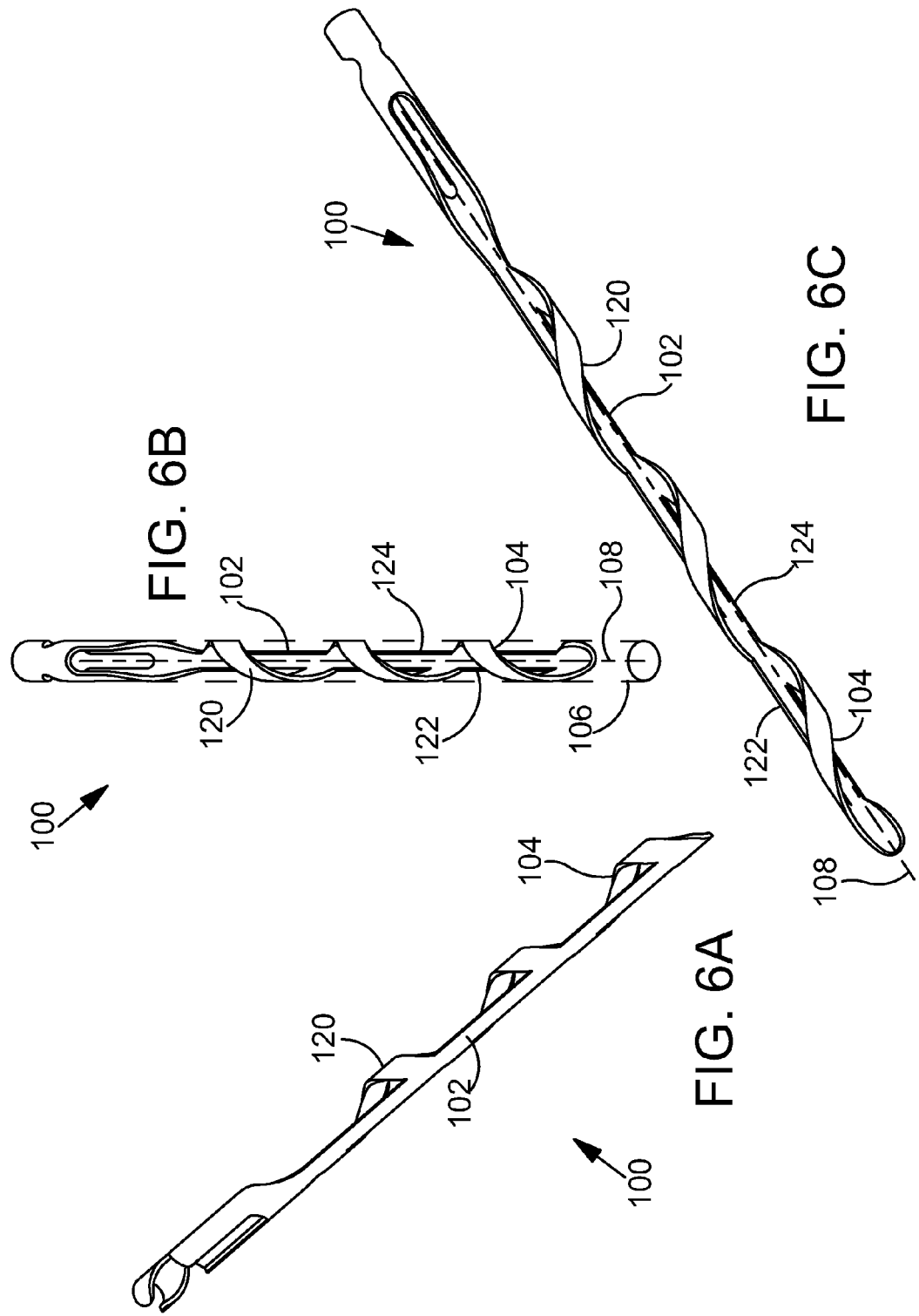
FIGS. 6A-6C are perspective views illustrating an exemplary ocular implant in accordance with the detailed description.

FIGS. 6A-6C are perspective views illustrating an exemplary ocular implant 100 in accordance with the present detailed description. FIGS. 6A-6C may be collectively referred to as FIG. 6. With reference to FIG. 6, it will be appreciated that ocular implant 100 may assume various orientations without deviating from the spirit and scope of this detailed description. Ocular implant 100 of FIG. 6, comprises a spine 102 and a plurality of curved supports 104 extending from spine 102. In FIGS. 6B and 6C, spine 102 and supports 104 can be seen extending along a longitudinal central axis 108 of ocular implant 100.

Supports 104 and spine 102 define a volume 106 that extends along axis 108 of ocular implant 100. Volume 106 is illustrated with dashed lines in FIG. 6B. In the embodiment of FIG. 6 volume 106 has a profile in a plane transverse to longitudinal central axis 108 that substantially corresponds to a circle with a diameter between 0.005 inches and 0.04 inches. The generally circular cross-sectional shape of volume 106 can be seen best in FIG. 6B. Ocular implant 100 can be made, for example, by laser cutting supports 104 and spine 102 from a length of metal (e.g., nitinol) tubing.

In the embodiment of FIG. 6, each support 104 comprises a loop 120. A first end of each loop 120 extends from a first side 122 of spine 102 and a second end of each loop 120 extends from a point on the second side 124 of spine 102 proximal to its intersection with the first end of loop 120 to form a portion of a helix. Adjacent pairs of loops 120 are held in a spaced apart relationship by spine portion 102. In the exemplary embodiment of FIG. 6, loops 120 are arranged so that no two loops 120 cross each other. With reference to FIG. 6, it will be appreciated that loops 120 are arranged along spine 102 to collectively form a helix. Loops 120 may, however, be arranged in other configurations without deviating from the spirit and scope of this detailed description.

An exemplary method in accordance with this detailed description may include the step of advancing the distal end of a cannula through the cornea of a human eye so that a distal portion of the cannula is disposed in the anterior chamber of the eye. The cannula may then be used to access Schlemm's canal of the eye, for example, by piercing the wall of Schlemm's canal with the distal end of the cannula. A distal opening of the cannula may be placed in fluid communication with a lumen defined by Schlemm's canal. An ocular implant may be advanced out of the distal opening of the cannula and into Schlemm's canal. The ocular implant may be configured to maximize ease of advancement and to minimize any trauma incurred by eye tissues during the delivery procedure. The ocular implant may also be configured to facilitate the flow of aqueous humor out of the anterior chamber of the eye after delivery into Schlemm's canal. The ocular implant may be designed to include various features that promote these aspects of performance. In some cases, however, features which improve one aspect of performance may have a detrimental impact on another aspect of performance. When this is the case, design tradeoffs may be made between competing performance considerations.

It is contemplated that an ocular implant may be advanced into Schlemm's canal using translational and/or rotational movement. In the exemplary embodiment of FIG. 6, the helical shape of support portion 104 may cause ocular implant 100 to advance into Schlemm's canal as it is rotated. In this way, the helical shape of support portion 104 may facilitate delivery of the ocular implant into Schlemm's canal and serve to minimize any trauma incurred by eye tissues during the delivery procedure.

In the exemplary embodiment of FIG. 6, ocular implant 100 has a generally circular cross-sectional shape. Advancing an ocular implant having a generally circular cross-sectional shape into Schlemm's canal may stretch the trabecular meshwork in a way that makes the trabecular meshwork more permeable. Making the trabecular meshwork more permeable may facilitate the flow of aqueous humor out of the anterior chamber. An ocular implant having a generally circular cross-sectional shape may also provide advantageous fluid flow characteristics for axial flow along the length of Schlemm's canal.

With particular reference to FIG. 6A, it will be appreciated that spine 102 of ocular implant 100 is uninterrupted by any openings so that spine 102 provides a continuous surface along its length. A spine having a continuous surface, uninterrupted by any openings, may serve to minimize any trauma incurred by the tissues of Schlemm's canal as ocular implant 100 is advanced into Schlemm's canal during a delivery procedure. In alternative embodiments, the spine may have one or more openings.

In the exemplary embodiment of FIG. 6, the width and thickness of spine 102 are selected so that implant 100 bends preferentially in a preferential bending plane. The preferential bending exhibited by ocular implant 100 may enhance the ability of the ocular implant to follow the lumen of Schlemm's canal during a delivery procedure. The lumen-seeking tendency provided by this arrangement may facilitate delivery of the ocular implant into Schlemm's canal and serve to minimize any trauma incurred by eye tissues during the delivery procedure.

Figure 7:
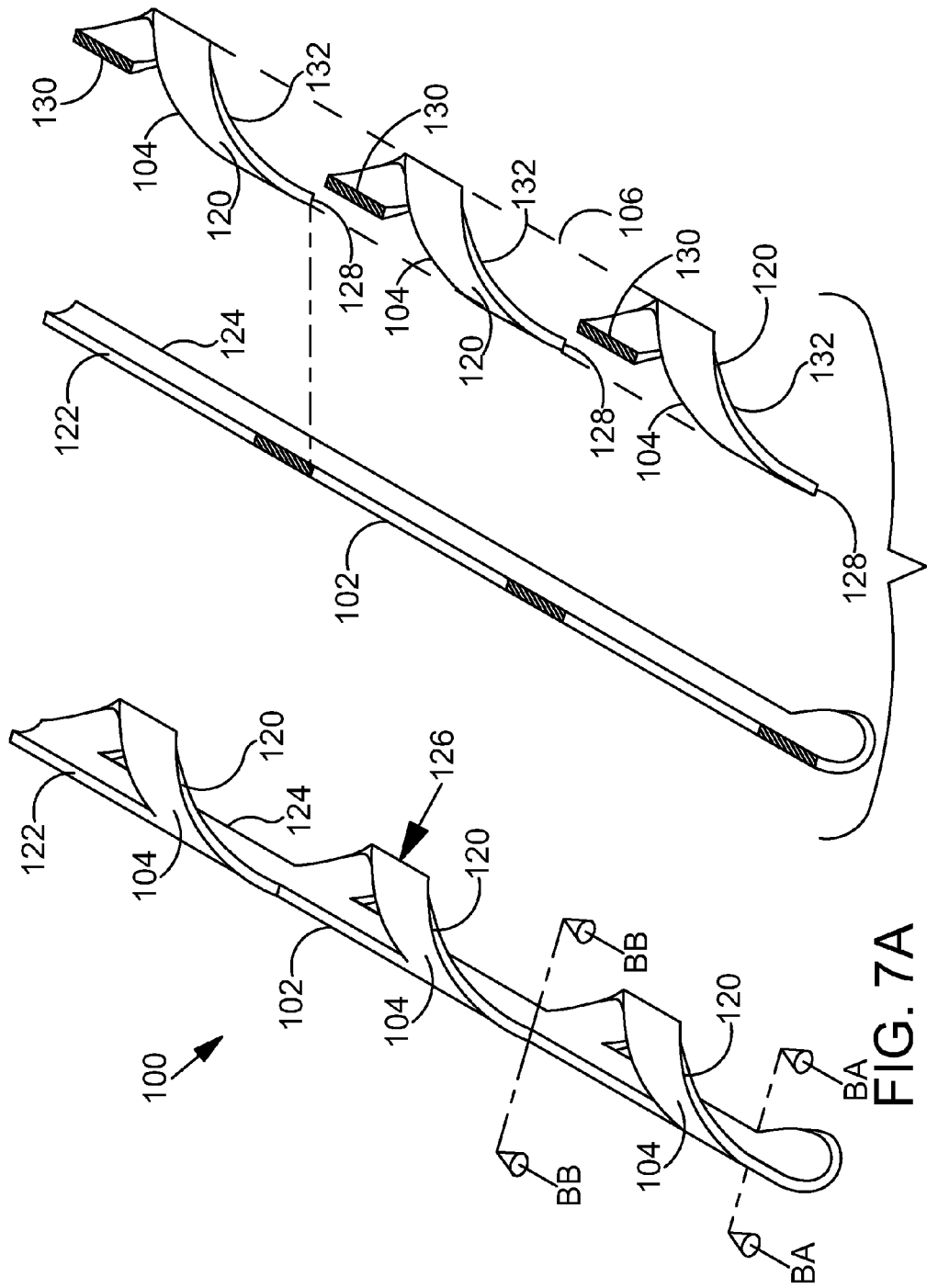
FIG. 7A is a perspective view showing a distal portion of the ocular implant shown in the previous figure. Two section lines BA-BA and BB-BB are illustrated with dashed lines in FIG. 7A.
FIG. 7B is a sectioned perspective view showing the ocular implant of FIG. 7A in an exploded state with cuts made along section lines BA-BA and BB-BB.

FIG. 7A is a perspective view showing a distal portion of ocular implant 100 shown in the previous figure. Two section lines BA-BA and BB-BB are illustrated with dashed lines in FIG. 7A. FIG. 7B is a sectioned perspective view showing ocular implant 100 of FIG. 7A in an exploded state. FIGS. 7A and 7B may be collectively referred to as FIG. 7.

Figure 8:
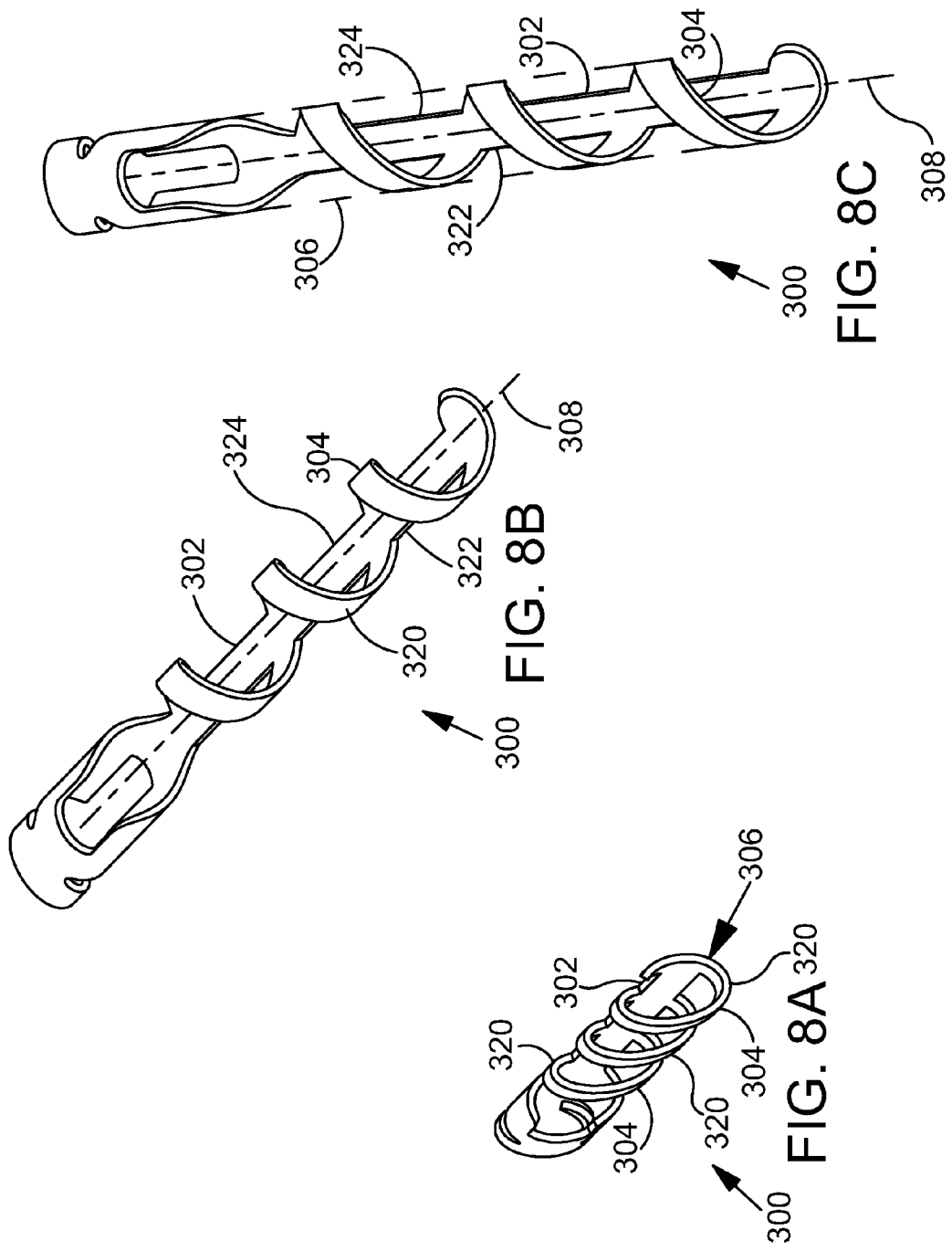
FIGS. 8A-8C are perspective views illustrating another exemplary ocular implant in accordance with the detailed description.

FIGS. 8A-8C are perspective views illustrating another exemplary ocular implant 300 in accordance with this detailed description. FIGS. 8A-8C may be collectively referred to as FIG. 8. Ocular implant 300 of FIG. 8, comprises a spine 302 and a plurality of curved supports 304 extending from spine 302. In FIGS. 8B and 8C, spine 302 and supports 304 can be seen extending along a longitudinal central axis 308 of ocular implant 300. Supports 304 and spine 302 define a volume 306 that extends along axis 308 of ocular implant 300. Volume 306 is illustrated with dashed lines in FIG. 8C.

In some useful embodiments, an ocular implant defines a volume having a generally ovoid or elliptical shape in lateral cross-section. With particular reference to FIG. 8A, it will be appreciated that volume 306 has a profile in a plane transverse to longitudinal central axis 308 that substantially corresponds to an ellipse having a maximum width between 0.005 inches and 0.04 inches. An ocular implant having a transverse cross-sectional shape that is similar to the transverse cross-sectional shape of Schlemm's canal (e.g., a generally ovoid or elliptical shape) may serve to minimize any trauma incurred by the tissues of Schlemm's canal as ocular implant 300 is advanced into Schlemm's canal during a delivery procedure. Additionally, an ocular implant having a generally ovoid or elliptical shape may seek a predetermined orientation within Schlemm's canal after the ocular implant has been delivered.

Ocular implant 300 can be made, for example, by laser cutting supports 304 and spine 302 from a length of metal (e.g., nitinol) tubing. The tubing may have a circular cross-sectional shape during the cutting process and deforming forces may be applied to the resulting part to produce the generally elliptical cross-sectional shape shown in FIG. 8. With reference to FIG. 8, it will be appreciated that ocular implant 300 may assume various orientations without deviating from the spirit and scope of this detailed description.

In the embodiment of FIG. 8, each support 304 comprises a loop 320. A first end of each loop 320 extends from a first side 322 of spine 302 and a second end of each loop 320 extends from a point on the second side 324 of spine 302 proximal to its intersection with the first end of loop 320 to form a portion of a helix. Adjacent pairs of loops 320 are held in a spaced apart relationship by spine 302. In the exemplary embodiment of FIG. 8, loops 320 are arranged so that no two loops 320 cross each other. With reference to FIG. 8, it will be appreciated that the first and second ends of loops 320 are arranged along spine 302 to collectively form a helix. It will also be appreciated that loops 320 may be arranged in other configurations without deviating from the spirit and scope of this detailed description.

An exemplary method in accordance with this detailed description may include the step of advancing an ocular implant (e.g., ocular implant 300 of FIG. 8) into Schlemm's canal of a human eye. The ocular implant may be configured to facilitate the flow of aqueous humor out of the anterior chamber, configured to facilitate delivery of the ocular implant into Schlemm's canal, and configured to minimize any trauma incurred by eye tissues during the delivery procedure. The ocular implant may be designed to include various features that promote these aspects of performance. In some cases, however, features which improve one aspect of performance may have a detrimental impact on another aspect of performance. When this is the case, design tradeoffs may be made between competing performance considerations.

It is contemplated that an ocular implant may be advanced into Schlemm's canal using translational and/or rotational movement. In the exemplary embodiment of FIG. 8, the helical shape of supports 304 may cause ocular implant 300 to advance into Schlemm's canal as it is rotated. Rotating ocular implant 300 as it advances into Schlemm's canal may also produce an alternating stretching and relaxing action that works the trabecular meshwork. Working the trabecular meshwork in this fashion may increase the permeability of the trabecular meshwork. Making the trabecular meshwork more permeable may facilitate the flow of aqueous humor out of the anterior chamber.

In the exemplary embodiment of FIG. 8, the width and thickness of spine 302 are selected so that implant 300 bends preferentially in a preferential bending plane. The preferential bending exhibited by ocular implant 300 may enhance the ability of the ocular implant to follow the lumen of Schlemm's canal during a delivery procedure. The lumen-seeking tendency provided by this arrangement may facilitate delivery of the ocular implant into Schlemm's canal and serve to minimize any trauma incurred by eye tissues during the delivery procedure.

Figure 9:
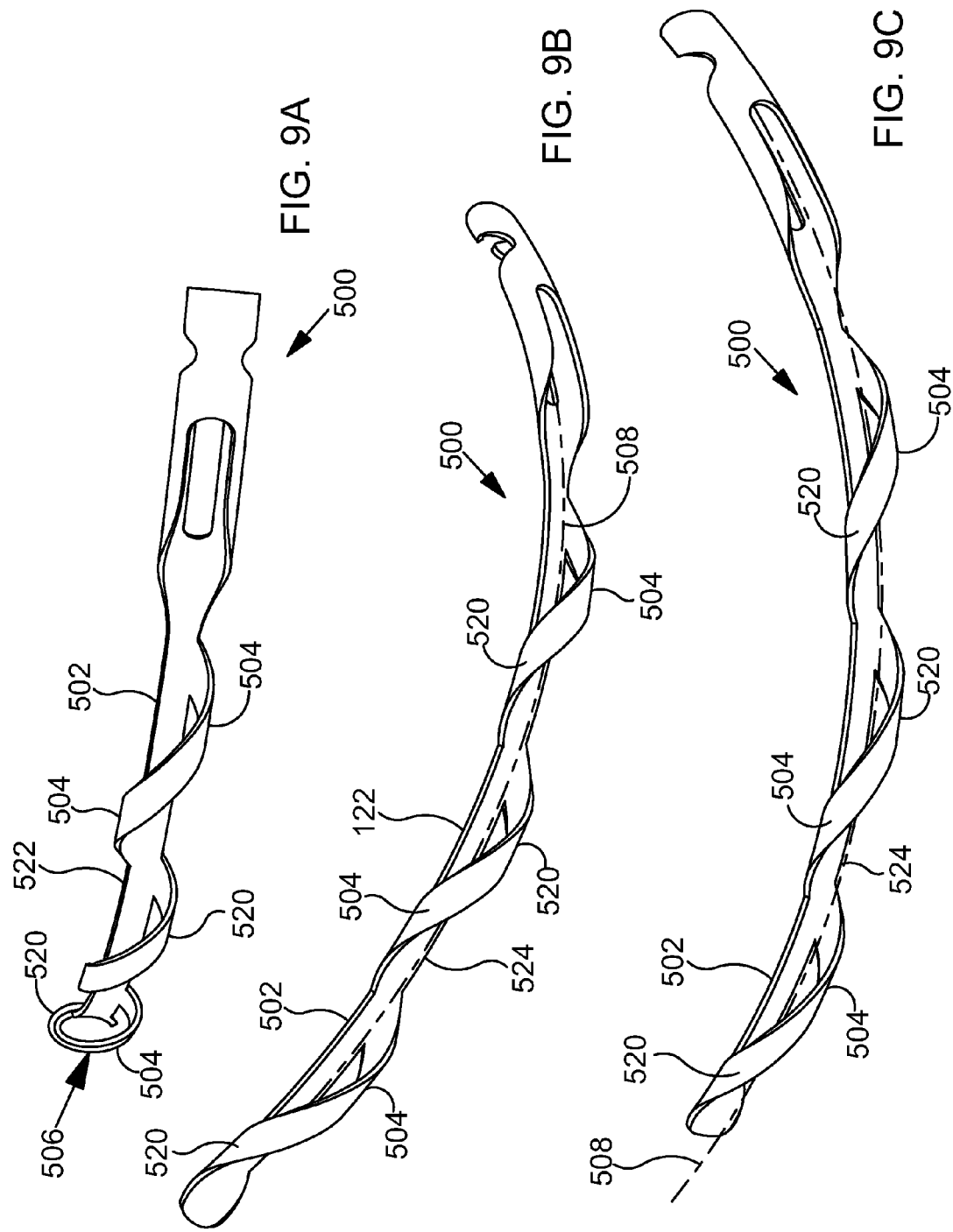
FIGS. 9A-9C are perspective views illustrating an additional exemplary ocular implant in accordance with the detailed description.

FIGS. 9A-9C are perspective views illustrating an additional exemplary ocular implant 500 in accordance with the present detailed description. FIGS. 9A-9C may be collectively referred to as FIG. 9. Ocular implant 500 of FIG. 9, comprises a spine 502 and a plurality of curved supports 504 extending from spine 502. In FIG. 9, spine 502 and supports 504 can be seen extending along a longitudinal central axis 508 of ocular implant 500. With reference to FIG. 9, it will be appreciated that longitudinal central axis 508 follows a curved path.

In the exemplary embodiment of FIG. 9, implant 500 is configured to bend preferentially in a preferential bending plane that is co-planar with a plane of curvature defined by longitudinal central axis 508. The preferential bending exhibited by ocular implant 500 may enhance the ability of the ocular implant to follow the lumen of Schlemm's canal during a delivery procedure. The curved shape of ocular implant 500 may also enhance the ability of the ocular implant to follow the lumen of Schlemm's canal during such a procedure. The lumen-seeking tendencies provided by this arrangement may facilitate delivery of the ocular implant into Schlemm's canal and serve to minimize any trauma incurred by eye tissues during the delivery procedure.

Supports 504 and spine 502 define a volume 506 that extends along axis 508 of ocular implant 500. In some useful embodiments, volume 506 has a generally ovoid or elliptical shape in lateral cross-section having a maximum width between 0.005 inches and 0.04 inches, as shown in the exemplary embodiment of FIG. 9. An ocular implant having a transverse cross-sectional shape that is similar to the transverse cross-sectional shape of Schlemm's canal (e.g., a generally ovoid or elliptical shape) may serve to minimize any trauma incurred by the tissues of Schlemm's canal as it is advanced into Schlemm's canal during a delivery procedure. Additionally, an ocular implant having a generally ovoid or elliptical shape may seek a predetermined orientation within Schlemm's canal after the ocular implant has been delivered. With reference to FIG. 9, it will be appreciated that ocular implant 500 may assume various orientations without deviating from the spirit and scope of this detailed description.

In the embodiment of FIG. 9, each support 504 comprises a curved loop 520. In FIG. 9, each loop 520 can be seen extending between a first side 522 of spine 502 and a point on a second side 524 of spine 502 proximal to its intersection with the first end of loop 520 to form a portion of a helix. Adjacent pairs of loops 520 are held in a spaced apart relationship by spine 502. In the exemplary embodiment of FIG. 9, loops 520 are arranged so that no two loops 520 cross each other. With reference to FIG. 9, it will be appreciated that the first side 522 and the second side 524 of loops 520 of FIG. 9 are arranged along spine 502 to collectively form a helix. It is contemplated that loops 520 may be arranged in other configurations without deviating from the spirit and scope of this detailed description.

Figure 10:
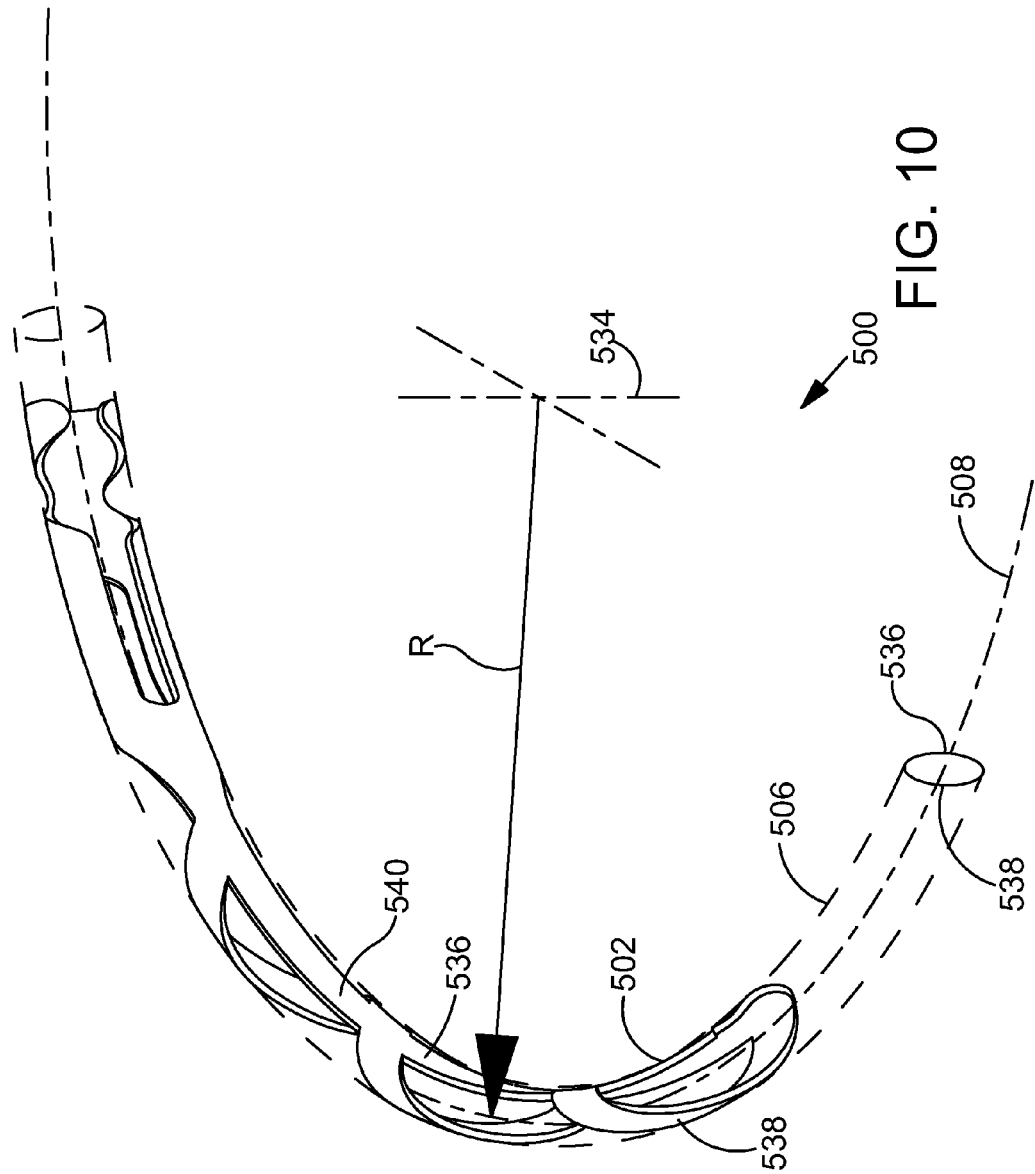
FIG. 10 is a perspective view showing an exemplary ocular implant in accordance with the detailed description.

FIG. 10 is an additional perspective view of ocular implant 500 shown in the previous figure. In the embodiment of FIG. 10, longitudinal central axis 508 follows a path that is generally curved, as stated above. A radius R of longitudinal central axis 508 is illustrated with an arrow in FIG. 10. The arrow illustrating radius R can be seen extending between a first lateral central axis 534 and longitudinal central axis 508 in FIG. 10. It is contemplated that radius R may be constant or may vary along the length of the longitudinal central axis. Volume 506 has an inner major side 536 (i.e., the radially inner surface of volume 506 corresponding to major axis 550 shown in FIG. 11B) and an outer major side 538 (i.e., the radially outer surface corresponding to major axis 550). Relative to radius R, inner major side 536 of volume 506 is disposed on a radially inward side of longitudinal central axis 508. Outer major side 538 of volume 506 is disposed on a radially outward side of longitudinal central axis 508 relative to radius R. With reference to FIG. 10, it will be appreciated that inner major side 536 is closer to the first lateral central axis 534 than outer major side 538.

Ocular implants in accordance with this detailed description may be delivered into Schlemm's canal of a patient's eye. The ocular implants may be configured to facilitate the flow of aqueous humor out of the anterior chamber when placed in Schlemm's canal. The ocular implants may also be configured to facilitate advancement into Schlemm's canal and to minimize any trauma incurred by eye tissues during the delivery procedure. The ocular implants may be designed to include various features that promote these aspects of performance. In some cases, however, features which improve one aspect of performance may have a detrimental impact on another aspect of performance. When this is the case, design tradeoffs may be made between competing performance considerations.

When placed in Schlemm's canal, ocular implant 500 of FIG. 10 will tend to assume an orientation in which spine portion 502 is offset from the outer major wall of Schlemm's canal and aligned with a central portion of the inner major side of Schlemm's canal. Spine portion 502 of ocular implant 500 is aligned with a central portion 540 of inner major side 536 of volume 506. Spine portion 502 is also disposed in a location offset from outer major side 538 of volume 506 in the embodiment of FIG. 10. Positioning the spine portion in a location offset from the outer major wall of Schlemm's canal may serve to minimize the likelihood that the ocular implant will obstruct collector channels. Aligning the spine portion of the ocular implant with a central portion of the inner major wall of Schlemm's canal may provide good support for the trabecular meshwork. Accordingly, it will be appreciated that the arrangement shown in FIG. 10 will facilitate the flow of aqueous humor out of the anterior chamber of the eye.

FIG. 11A is an additional perspective view showing volume 506 defined by the ocular implant shown in the previous figure. With reference to FIG. 11A, it will be appreciated that volume 506 extends along longitudinal central axis 508.

Figure 11:
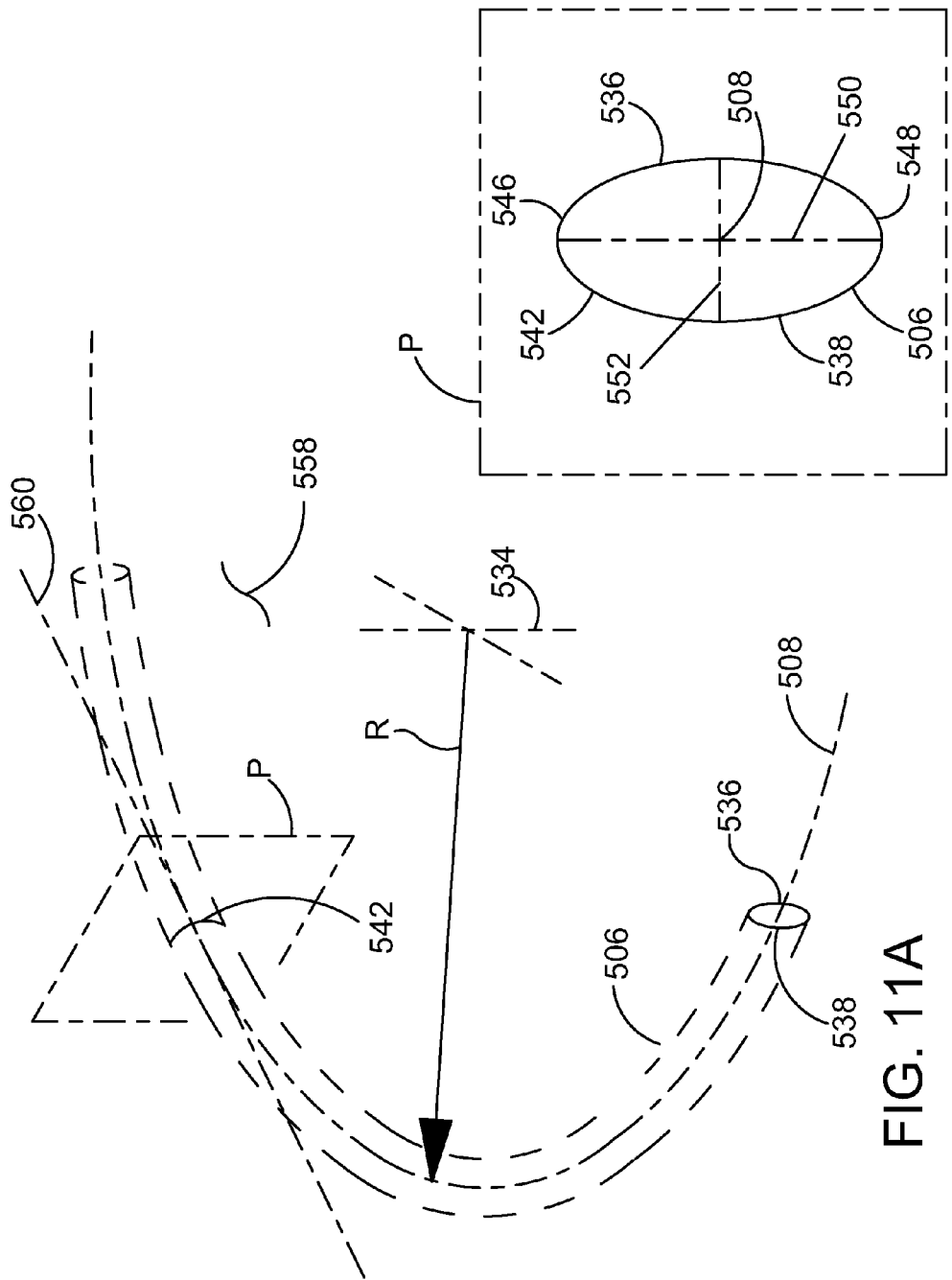
FIG. 11A is an additional perspective view showing the volume defined by a plurality of support portions of the ocular implant shown in the previous figure.
FIG. 11B is a plan view further illustrating a profile of the volume defined by the ocular implant.

Longitudinal central axis 508 defines a curvature plane 558 in the embodiment of FIG. 11. An exemplary plane P is shown intersecting volume 506 in FIG. 11A. Plane P is generally transverse to volume 506 and longitudinal central axis 508. More particularly, in the exemplary embodiment of FIG. 11A, plane P is orthogonal to a reference line 560 that lies in curvature plane 558 and is tangent to longitudinal central axis 508. In the embodiment of FIG. 11, volume 506 has a profile 542 that lies in plane P.

FIG. 11B is a plan view further illustrating plane P and profile 542 of volume 506 shown in FIG. 11A. With reference to FIG. 11B, it will be appreciated that volume 506 has a first minor side 546 that extends between inner major side 536 and outer major side 538. A second minor side 548 of volume 506 is shown extending between inner major side 536 and outer major side 538 in FIG. 11B. A major lateral axis 550 and a minor lateral axis 552 of volume 506 are illustrated with dashed lines in FIG. 11B. With reference to FIG. 11B, it will be appreciated that major lateral axis 550 is longer than minor lateral axis 552.

In some useful embodiments, profile 542 has a generally ovoid or elliptical shape in lateral cross-section. In the exemplary embodiment of FIG. 11B, profile 542 has a shape generally corresponding to the shape of an ellipse. In the exemplary embodiment of FIG. 11, inner major side 536 is longer than both first minor side 546 and second minor side 548. Also in the exemplary embodiment of FIG. 11, outer major side 538 is longer than both first minor side 546 and second minor side 548. An ocular implant having a transverse cross-sectional shape that is similar to the transverse cross-sectional shape of Schlemm's canal (e.g., a generally ovoid or elliptical shape) may serve to minimize any trauma incurred by the tissues of Schlemm's canal as ocular implant 500 is advanced into Schlemm's canal during a delivery procedure. Additionally, an ocular implant having a generally ovoid or elliptical shape may seek a predetermined orientation within Schlemm's canal after the ocular implant has been delivered.

FIG. 12A is an additional perspective view showing ocular implant 500. Ocular implant 500 is shown extending along a longitudinal central axis 508 in FIG. 12A. A first plane 554 and a second plane 556 are shown intersecting ocular implant 500 in FIG. 12A. In the embodiment of FIG. 12A, longitudinal central axis 508 follows a path that is generally curved such that longitudinal central axis 508 defines a plane of curvature that is co-planar with first plane 554 shown in FIG. 12A.

Ocular implant 500 of FIG. 12A comprises a spine 502 carrying a plurality of supports 504. With reference to FIG. 12A, it will be appreciated that first plane 554 intersects spine 502 of ocular implant 500. In the embodiment of FIG. 12A, first plane 554 bisects spine 502 into two halves. In the embodiment of FIG. 12A, the two halves of spine 502 are symmetrically shaped about first plane 554. With reference to FIG. 12A, it will be appreciated that supports 504 of ocular implant 500 are not symmetric about first plane 554.

In the embodiment of FIG. 12A, the flexibility of implant 500 is at a maximum when implant 500 is bending along first plane 554, and implant 500 has less flexibility when bending along a plane other than first plane 554 (e.g., a plane that intersects first plane 554). Accordingly, first plane 554 may be referred to as a plane of preferential bending. In the embodiment shown in FIG. 12A, for example, implant 500 has a second flexibility when bending along second plane 556 that is less than the first flexibility that implant 500 has when bending along first plane 554. Stated another way, in the embodiment of FIG. 12A, the bending modulus of implant 500 is at a minimum when implant 500 is bent along first plane 554. Implant 500 has a first bending modulus when bent along first plane 554 and a greater bending modulus when bent along a plane other than first plane 554 (e.g., a plane that intersects first plane 554). For example, in the embodiment shown in FIG. 12A, implant 500 has a second bending modulus when bent along second plane 556 that is greater than the first bending modulus that implant 500 has when bent along first plane 554.

In the exemplary embodiment of FIG. 11, implant 500 is configured to bend preferentially in a preferential bending plane that is co-planar with first plane 554. The preferential bending exhibited by ocular implant 500 may enhance the ability of the ocular implant to follow the lumen of Schlemm's canal during a delivery procedure. The curved shape of ocular implant 500 may also enhance the ability of the ocular implant to follow the lumen of Schlemm's canal during such a procedure. The lumen-seeking tendencies provided by this arrangement may facilitate delivery of the ocular implant into Schlemm's canal and serve to minimize any trauma incurred by eye tissues during the delivery procedure.

Second plane 556 is transverse to ocular implant 500 and longitudinal central axis 508 in the embodiment of FIG. 12A. More particularly, in the exemplary embodiment of FIG. 12A, second plane 556 is orthogonal to a reference line 560 that lies in first plane 554 and is tangent to longitudinal central axis 508.

FIG. 12B is a plan view further illustrating second plane 556 shown in FIG. 12B. With reference to FIG. 12B, it will be appreciated that spine portion 502 has a lateral cross-sectional shape S that lies in second plane 556. First plane 554 is shown intersecting lateral cross-sectional shape S in FIG. 12B. In the embodiment of FIG. 12A, first plane 554 bisects spine portion 502 into two halves. In the embodiment of FIG. 12A, the two halves of spine portion 502 are symmetrically shaped about first plane 554.

Figure 12:
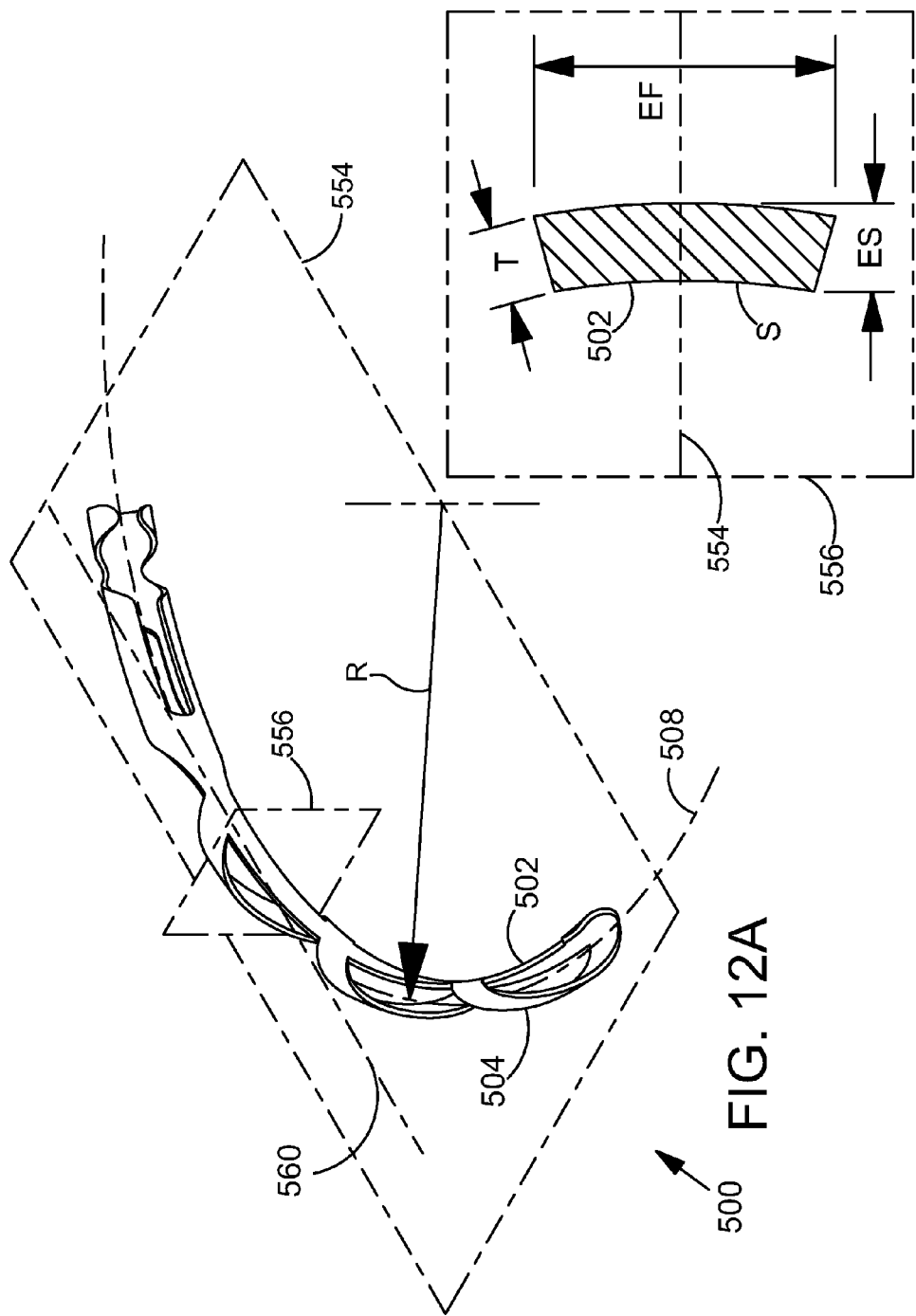
FIG. 12A is an additional perspective view showing the ocular implant shown in FIG. 10.
FIG. 12B is an enlarged plan view further illustrating a lateral cross-sectional shape of a spine portion of the ocular implant.

As shown in FIG. 12, spine portion 502 of ocular implant 500 has a first lateral extent EF and a second lateral extent ES. Spine portion 502 is configured to preferential bend along first plane 554 in the embodiment of FIG. 12. In some useful embodiments, first lateral extent EF is greater than second lateral extent ES. In some useful embodiments, the aspect ratio of first lateral extent EF to second lateral extent ES is greater than about three.

With reference to FIG. 12B, it will be appreciated that spine portion 502 has a thickness T. In some useful embodiments, an aspect ratio of first lateral extent EF to thickness T is greater than about one. In some useful embodiments, the aspect ratio of first lateral extent EF to thickness T is greater than about three.

Figure 13:
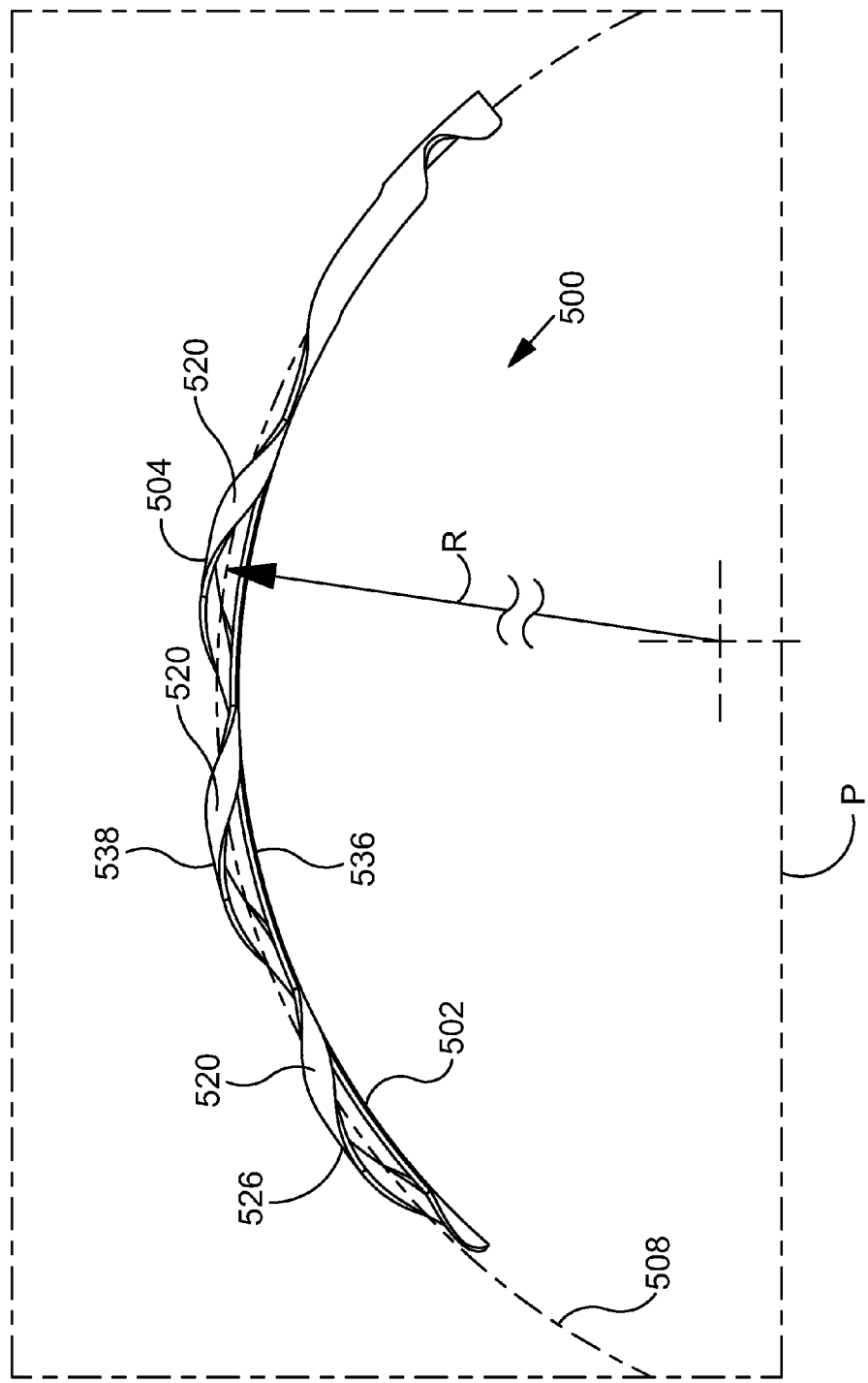
FIG. 13 is a plan view of the ocular implant shown in the previous figure.

FIG. 13 is a plan view of ocular implant 500 shown in the previous figure. Ocular implant 500 of FIG. 13 has a generally curved shape. In the embodiment of FIG. 13, a curved longitudinal central axis 508 of ocular implant 500 defines a plane P. A radius R of longitudinal central axis 508 is illustrated with an arrow in FIG. 13. It will be appreciated that that radius R may be constant or may vary along the length of longitudinal central axis 508 of ocular implant 500.

Ocular implant 500 of FIG. 13 has an inner side 536 and an outer side 538. Relative to radius R, inner side 536 of ocular implant 500 is disposed on a radially inward side of longitudinal central axis 508. Outer side 538 of ocular implant 500 is disposed on a radially outward side of longitudinal central axis 508 relative to radius R. In FIG. 13, inner side 536 has a concave shape and outer side 538 has a convex shape. Accordingly, inner side 536 may be referred to as a longitudinally concave side of ocular implant 500. Outer side 538 may be referred to as a longitudinally convex side of ocular implant 500. With reference to FIG. 13, it will be appreciated that spine portion 502 is located on the longitudinally concave side of ocular implant 500.

Figure 14:
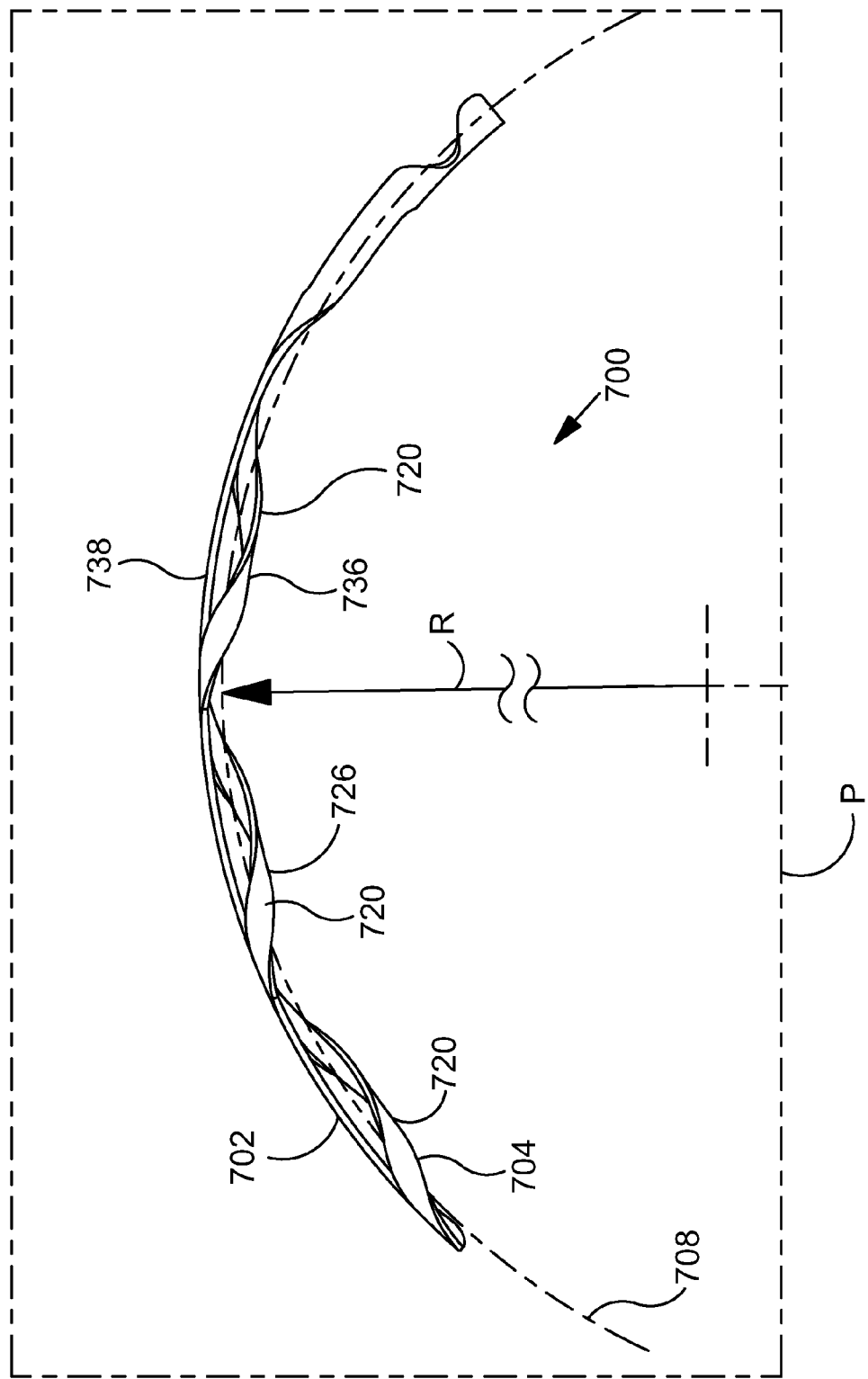
FIG. 14 is a plane view showing an exemplary ocular implant in accordance with the detailed description.

FIG. 14 is a plan view showing an exemplary ocular implant 700 in accordance with this detailed description. Ocular implant 700 of FIG. 14 has a generally curved shape. In the embodiment of FIG. 14, a curved longitudinal central axis 708 of ocular implant 700 defines a plane P. A radius R of longitudinal central axis 708 is illustrated with an arrow in FIG. 14. It is contemplated that radius R may be constant or may vary along the length of longitudinal central axis 708.

Ocular implant 706 of FIG. 14 has an inner side 736 and an outer side 738. Relative to radius R, inner side 736 of volume 706 is disposed on a radially inward side of longitudinal central axis 708. Outer side 738 of volume 706 is disposed on a radially outward side of longitudinal central axis 708 relative to radius R. In FIG. 14, inner side 736 has a concave shape and outer side 738 has a convex shape. Accordingly, inner side 736 may be referred to as a longitudinally concave side of ocular implant 700. Outer side 738 may be referred to as a longitudinally convex side of ocular implant 700.

Ocular implant 700 of FIG. 14 comprises a spine 702 from which a plurality of supports 704 extend. In FIG. 14, spine 702 and supports 704 can be seen extending along longitudinal central axis 708 of ocular implant 700. With reference to FIG. 14, it will be appreciated that spine 702 is located on the longitudinally convex side of ocular implant 700.

Supports 704 and spine 702 of ocular implant 700 define a volume 706 that extends along axis 708 of ocular implant 700. In the embodiment of FIG. 14, each support 104 comprises a loop 720. With reference to FIG. 14, it will be appreciated that loops 720 of FIG. 14 are arranged along spine 702 to form a helix 726. Each loop forms a turn of helix 726 in the embodiment of FIG. 14. Adjacent turns of helix 726 are held in a spaced apart relationship by spine portion 702.

An exemplary method in accordance with this detailed description may include the step of advancing an ocular implant (e.g., ocular implant 700 of FIG. 14) into Schlemm's canal of a human eye. The ocular implant may be configured to facilitate the flow of aqueous humor out of the anterior chamber, configured to facilitate delivery of the ocular implant into Schlemm's canal, and configured to minimize any trauma incurred by eye tissues during the delivery procedure. The ocular implant may be designed to include various features that promote these aspects of performance. In some cases, however, features which improve one aspect of performance may have a detrimental impact on another aspect of performance. When this is the case, design tradeoffs may be made between competing performance considerations.

An ocular implant including a spine located on a longitudinally convex side thereof (such as ocular implant 700) may enable the spine to slide against the outer major wall of Schlemm's canal as the ocular implant is advanced into Schlemm's canal. The spine may be supported by the scleral tissue of the eye that supports the outer major wall of Schlemm's canal. Accordingly, an ocular implant including a spine located on a longitudinally convex side thereof may reduce the trauma inflicted on the tissues of Schlemm's canal as the ocular implant is advanced into Schlemm's canal during a delivery procedure.

With reference to FIG. 14, it will be appreciated that spine 702 of ocular implant 700 is uninterrupted by any openings so that spine 702 provides a continuous surface along its length. A spine having a continuous surface, uninterrupted by any openings, may reduce the trauma inflicted on the tissues of Schlemm's canal as ocular implant 700 is advanced into Schlemm's canal during a delivery procedure. In alternative embodiments, the spine may have one or more openings.

Figure 15:
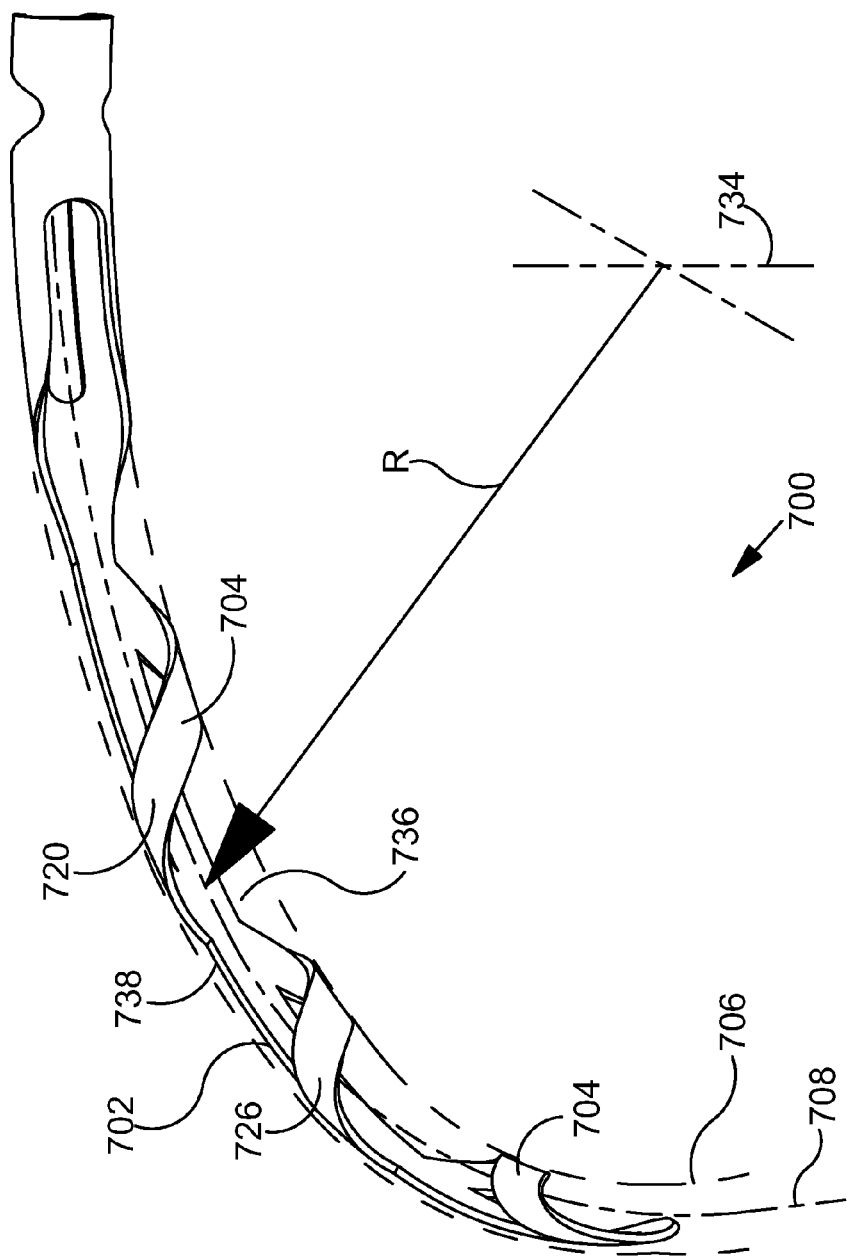
FIG. 15 is a perspective view showing the ocular implant shown in the previous figure.

FIG. 15 is a perspective view showing ocular implant 700 shown in the previous figure. In the embodiment of FIG. 15, longitudinal central axis 708 follows a path that is generally curved. A radius R of longitudinal central axis 708 is illustrated with an arrow in FIG. 15. Radius R may be constant or may vary along the length of the longitudinal central axis 708. In FIG. 15, the arrow illustrating radius R can be seen extending between a first lateral central axis 734 and longitudinal central axis 708. Volume 706 has an inner major side 736 and an outer major side 738. Relative to radius R, inner major side 736 of volume 706 is disposed on a radially inward side of longitudinal central axis 708. Outer major side 738 of volume 706 is disposed on a radially outward side of longitudinal central axis 708 relative to radius R. With reference to FIG. 15, it will be appreciated that inner major side 736 is closer to the first lateral central axis 734 than outer major side 738. With reference to FIG. 15, it will be appreciated that spine 702 is disposed in a location adjacent to a central portion of outer major side 738 of volume 706.

In the embodiment of FIG. 15, each support portion 704 comprises a curved loop 720. In FIG. 15, each loop 720 can be seen extending between a first side of spine 702 and a point on a second side of spine 702 proximal to the intersection of the loop with the first side of the spine to form a portion of a helix. Adjacent pairs of loops 720 are held in a spaced apart relationship by spine portion 702. In the exemplary embodiment of FIG. 15, loops 720 are arranged so that no two loops 720 cross each other. With reference to FIG. 15, it will be appreciated that loops 720 of FIG. 15 are arranged with respect to spine 702 to collectively form a helix 726. Loops 720 may, however, be arranged in other configurations without deviating from the spirit and scope of this detailed description.

Figure 16:
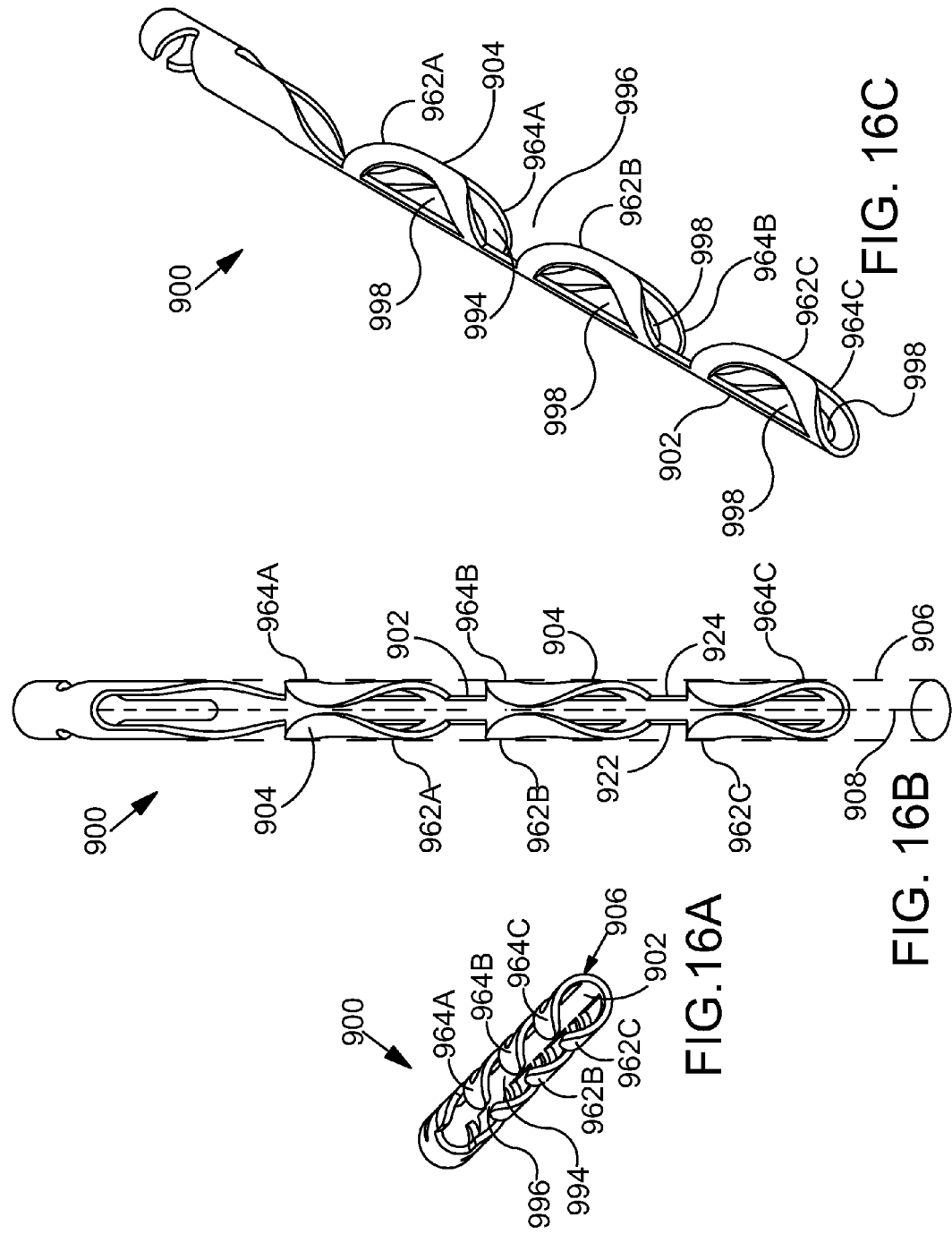
FIGS. 16A, 16B and 16C are perspective views illustrating an exemplary ocular implant in accordance with the detailed description.

FIGS. 16A-16C are perspective views illustrating an exemplary ocular implant 900 in accordance with the present detailed description. FIGS. 16A-16C may be collectively referred to as FIG. 16. With reference to FIG. 16, it will be appreciated that ocular implant 900 may assume various orientations without deviating from the spirit and scope of this detailed description. Ocular implant 900 of FIG. 16, comprises a spine 902 and a plurality of supports 904 extending from spine portion 902. In FIG. 16B, spine 902 and supports 904 can be seen extending along a longitudinal central axis 908 of ocular implant 900.

A volume 906 defined by supports 904 and spine 902 is illustrated with dashed lines in FIG. 16B. Volume 906 extends along longitudinal central axis 908 of ocular implant 900 and has a maximum width perpendicular to the longitudinal axis of between 0.005 inches and 0.04 inches. Supports 904 are held in a spaced apart relationship by spine 902. In the embodiment of FIG. 16, supports 904 include a plurality of dorsal loops 962 and a plurality of ventral loops 964. Each dorsal loop 962 has first end and a second end that are both affixed to first side 922 of spine 902. Openings 998 are disposed between the dorsal loops 962 and spine 902. Dorsal loops 962 of ocular implant 900 include a first dorsal loop 962A, a second dorsal loop 962B, and a third dorsal loop 962C.

Ventral loops 964 of ocular implant 900 include a first ventral loop 964A, a second ventral loop 964B, and a third ventral loop 964C. Each ventral loop 964 has first end and a second end that are both affixed to second side 924 of spine 902. Openings 998 are disposed between the ventral loops 964 and spine 902. In the exemplary embodiment of FIG. 16, the loops are arranged so that no two loops cross each other.

Ocular implant 900 defines a channel 994 that opens into an elongate channel opening 996. The channel extends along the length of spine 902. The channel opening is disposed opposite spine 902 such that the channel opens away from spine 902. With particular reference to FIG. 16B, it will be appreciated that the channel and the channel opening extend between first dorsal loop 962A and first ventral loop 964A. The channel and the channel opening also extend between second dorsal loop 962B and second ventral loop 964B. The channel and the channel opening can also been seen extending together between third dorsal loop 962C and third ventral loop 964C in FIG. 16B.

An exemplary method in accordance with this detailed description may include the step of advancing an ocular implant (e.g., ocular implant 900 of FIG. 16) into Schlemm's canal of a human eye. The ocular implant may be configured to facilitate the flow of aqueous humor out of the anterior chamber, configured to facilitate delivery of the ocular implant into Schlemm's canal, and configured to minimize any trauma incurred by eye tissues during the delivery procedure. The ocular implant may be designed to include various features that promote these aspects of performance. In some cases, however, features which improve one aspect of performance may have a detrimental impact on another aspect of performance. When this is the case, design tradeoffs may be made between competing performance considerations.

In the exemplary embodiment of FIG. 16, ocular implant 900 has a generally circular cross-sectional shape. With particular reference to FIG. 16A, it will be appreciated that volume 906 defined by supports 904 has a profile in a plane transverse to longitudinal central axis 908 that substantially corresponds to a circle. Ocular implant 900 can be made, for example, by laser cutting supports 904 and spine 902 from a length of metal (e.g., nitinol) tubing. Advancing an ocular implant having a generally circular cross-sectional shape into Schlemm's canal may stretch the trabecular meshwork in a way that makes the trabecular meshwork more permeable. Making the trabecular meshwork more permeable may facilitate the flow of aqueous humor out of the anterior chamber. An ocular implant having a generally circular cross-sectional shape may also provide advantageous fluid flow characteristics for axial flow along the length of Schlemm's canal.

With particular reference to FIG. 16A, it will be appreciated that spine 902 of ocular implant 900 is uninterrupted by any openings so that spine 902 provides a continuous surface along its length. A spine having a continuous surface, uninterrupted by any openings, may serve to minimize any trauma incurred by the tissues of Schlemm's canal as ocular implant 900 is advanced into Schlemm's canal during a delivery procedure.

Figure 17:
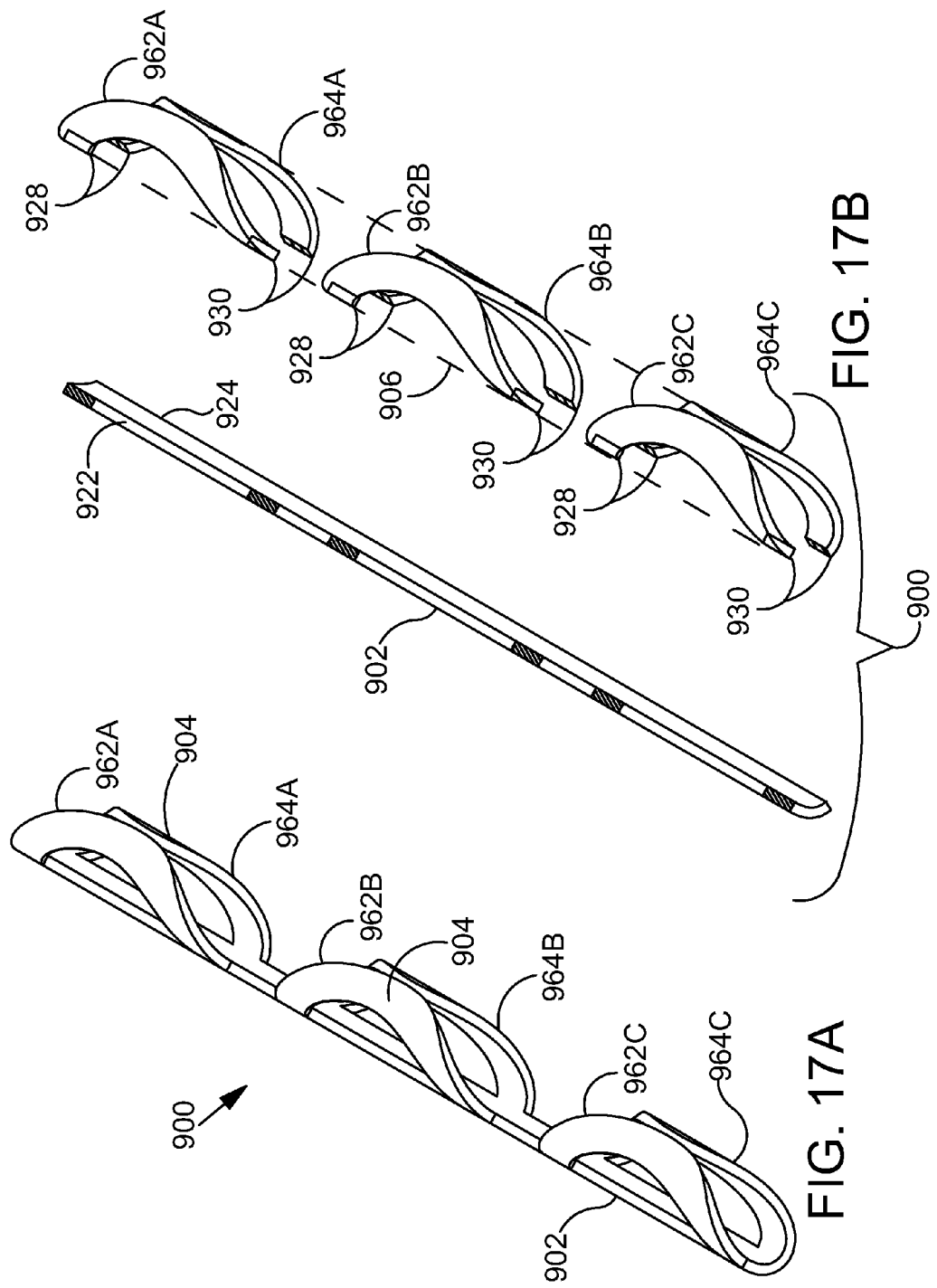
FIG. 17A is a perspective view showing a distal portion of the ocular implant shown in the previous figure. Two section lines BA-BA and BB-BB are illustrated with dashed lines in FIG. 17A.
FIG. 17B is a sectioned perspective view showing the ocular implant of FIG. 17A in an exploded state with cuts made along section lines BA-BA and BB-BB.

FIG. 17A is a perspective view showing a distal portion of ocular implant 900 shown in the previous figure. Two section lines BA-BA and BB-BB are illustrated with dashed lines in FIG. 17A. FIG. 17B is a sectioned perspective view showing ocular implant 900 of FIG. 17A in an exploded state. FIGS. 17A and 17B may be collectively referred to as FIG. 17.

Figure 18:
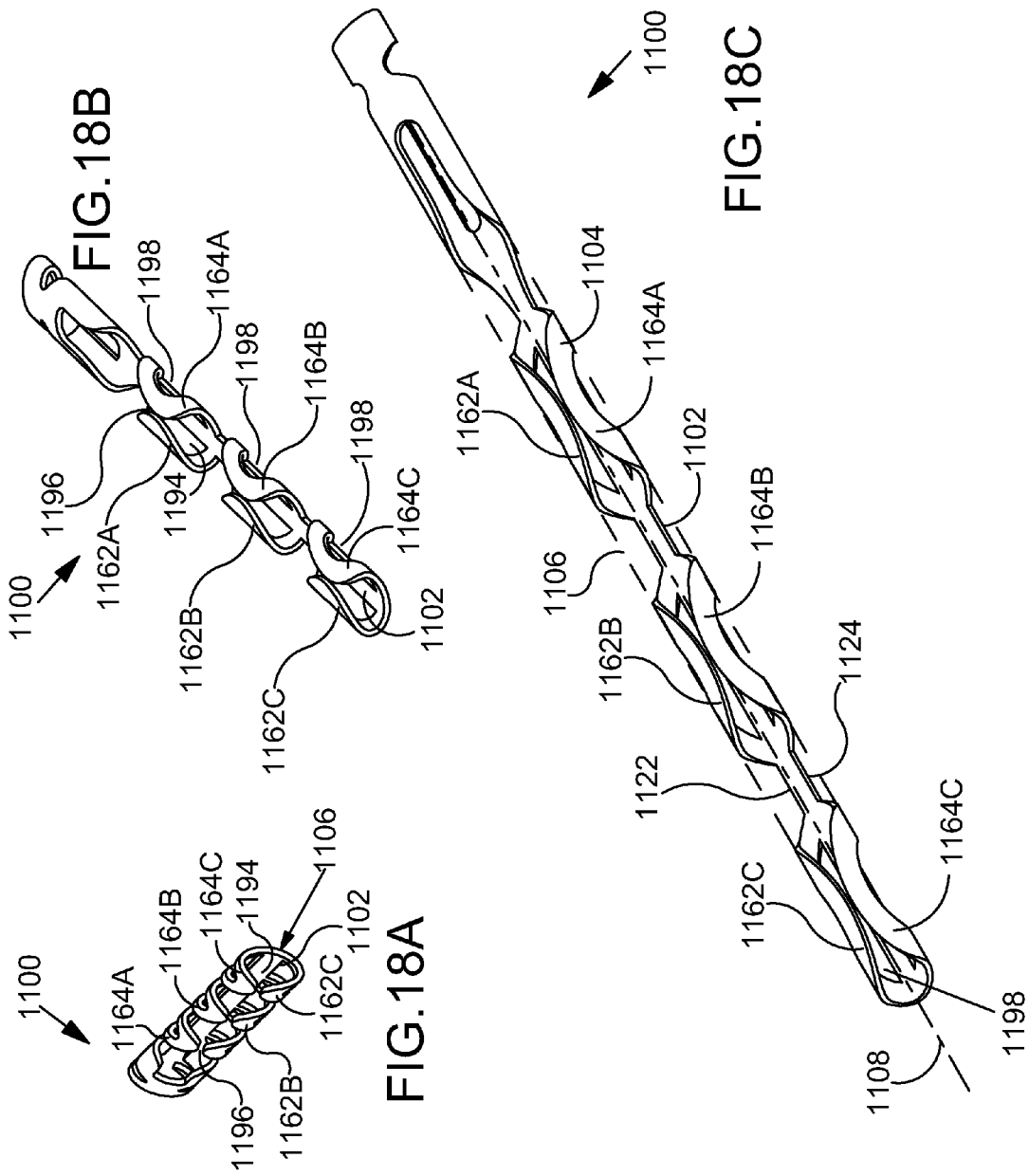
FIGS. 18A-18C are perspective views illustrating another exemplary ocular implant in accordance with the detailed description.

FIGS. 18A-18C are perspective views illustrating another exemplary ocular implant 1100 in accordance with this detailed description. FIGS. 18A-18C may be collectively referred to as FIG. 18. Ocular implant 1100 of FIG. 18, comprises a spine 1102 and a plurality of supports 1104 extending from spine 1102. In FIG. 18C, spine 1102 and supports 1104 can be seen extending along a longitudinal central axis 1108 of ocular implant 1100. Supports 1104 and spine 1102 define a volume 1106 that extends along spine axis 1108 of ocular implant 1100. Volume 1106 is illustrated with dashed lines in FIG. 18C and has a maximum width perpendicular to the longitudinal axis of between 0.005 inches and 0.04 inches.

In some useful embodiments, an ocular implant defines a volume having a generally ovoid or elliptical shape in lateral cross-section. With particular reference to FIG. 18A, it will be appreciated that volume 1106 has a profile in a plane transverse to longitudinal central axis 1108 that substantially corresponds to an ellipse. An ocular implant having a transverse cross-sectional shape that is similar to the transverse cross-sectional shape of Schlemm's canal (e.g., a generally ovoid or elliptical shape) may serve to minimize any trauma incurred by the tissues of Schlemm's canal as ocular implant 1100 is advanced into Schlemm's canal during a delivery procedure. Additionally, an ocular implant having a generally ovoid or elliptical shape may seek a predetermined orientation within Schlemm's canal after the ocular implant has been delivered.

Ocular implant 1100 can be made, for example, by laser cutting supports 1104 and spine 1102 from a length of metal (e.g., nitinol) tubing. The tubing may have a circular cross-sectional shape during the cutting process and deforming forces may be applied to the resulting part to produce the generally elliptical cross-sectional shape shown in FIG. 18. With reference to FIG. 18, it will be appreciated that ocular implant 1100 may assume various orientations without deviating from the spirit and scope of this detailed description.

Supports 1104 are held in a spaced apart relationship by spine 1102. In the embodiment of FIG. 111, supports 1104 include a plurality of dorsal loops 1162 and a plurality of ventral loops 1164. Each dorsal loop 1162 has first end and a second end that are both affixed to first side 1122 of spine 1102. Openings 1198 are disposed between the dorsal loops 1162 and spine 1102. Dorsal loops 1162 of ocular implant 1100 include a first dorsal loop 1162A, a second dorsal loop 1162B, and a third dorsal loop 1162C.

Ventral loops 1164 of ocular implant 1100 include a first ventral loop 1164A, a second ventral loop 1164B, and a third ventral loop 1164C. Each ventral loop 1164 has first end and a second end that are both affixed to second side 1124 of spine portion 1102. Openings 1198 are disposed between the ventral loops 1164 and spine 1102. In the exemplary embodiment of FIG. 111, the loops are arranged so that no two loops cross each other.

Ocular implant 1100 defines a channel 1194 that opens into an elongate channel opening 1196. The channel extends along the length of spine 1102. The channel opening is disposed opposite spine 1102 in the embodiment of FIG. 18. Accordingly, the channel may be said to open away from spine 1102. With particular reference to FIG. 18B, it will be appreciated that the channel and the channel opening extending together between first dorsal loop 1162A and first ventral loop 1164A. The channel and the channel opening also extend between second dorsal loop 1162B and second ventral loop 1164B. The channel and the channel opening can also been seen extending together between third dorsal loop 1162C and third ventral loop 1164C in FIG. 18B.

Figure 19:
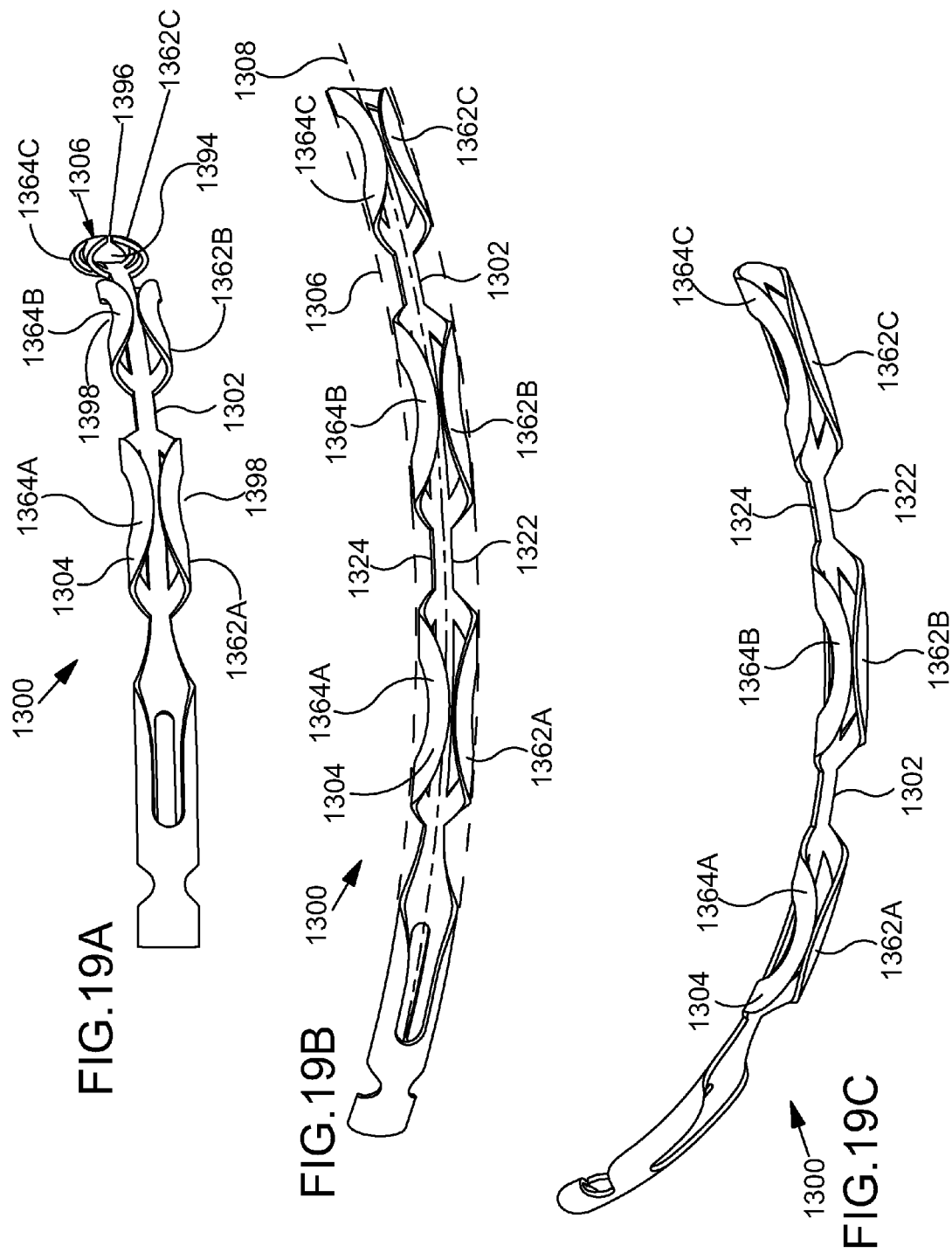
FIGS. 19A-19C are perspective views illustrating an additional exemplary ocular implant in accordance with the detailed description.

FIGS. 19A-19C are perspective views illustrating an additional exemplary ocular implant 1300 in accordance with the present detailed description. FIGS. 19A-19C may be collectively referred to as FIG. 19. Ocular implant 1300 of FIG. 19, comprises a spine 1302 and a plurality of supports 1304 extending from spine 1302. In FIG. 19A, spine 1302 and supports 1304 can be seen extending along a longitudinal central axis 1308 of ocular implant 1300. With reference to FIG. 19, it will be appreciated that longitudinal central axis 1308 follows a curved path.

In the exemplary embodiment of FIG. 19, ocular implant 1300 is configured to bend preferentially in a preferential bending plane that is co-planar with a plane of curvature defined by longitudinal central axis 1308. The preferential bending exhibited by ocular implant 1300 may enhance the ability of the ocular implant to follow the lumen of Schlemm's canal during a delivery procedure. The curved shape of ocular implant 1300 may also enhance the ability of the ocular implant to follow the lumen of Schlemm's canal during such a procedure. The lumen-seeking tendencies provided by this arrangement may facilitate delivery of the ocular implant into Schlemm's canal and serve to minimize any trauma incurred by eye tissues during the delivery procedure.

Supports 1304 and spine 1302 define a volume 1306 that extends along axis 1308 of ocular implant 1300. Volume 1306 is illustrated with dashed lines in FIG. 19. In some useful embodiments, volume 1306 has a generally ovoid or elliptical shape in lateral cross-section and has a maximum width perpendicular to the longitudinal axis of between 0.005 inches and 0.04 inches. In the exemplary embodiment of FIG. 19, volume 1306 has a profile in a plane transverse to ocular implant 1300 and longitudinal central axis 1308 that substantially corresponds to an ellipse. The generally elliptical shape of volume 1306 can be best seen in FIG. 19A. An ocular implant having a transverse cross-sectional shape that is similar to the transverse cross-sectional shape of Schlemm's canal (e.g., a generally ovoid or elliptical shape) may serve to minimize any trauma incurred by the tissues of Schlemm's canal as ocular implant 1300 is advanced into Schlemm's canal during a delivery procedure. Additionally, an ocular implant having a generally ovoid or elliptical shape may seek a predetermined orientation within Schlemm's canal after the ocular implant has been delivered. With reference to FIG. 19, it will be appreciated that ocular implant 1300 may assume various orientations without deviating from the spirit and scope of this detailed description.

Supports 1304 are held in a spaced apart relationship by spine 1302. In the embodiment of FIG. 13, supports 1304 include a plurality of dorsal loops 1362 and a plurality of ventral loops 1364. Each dorsal loop 1362 has first end and a second end that are both affixed to first side 1322 of spine portion 1302. Openings 1398 are disposed between the dorsal loops 1362 and spine 1302. Dorsal loops 1362 of ocular implant 1300 include a first dorsal loop 1362A, a second dorsal loop 1362B, and a third dorsal loop 1362C.

Ventral loops 1364 of ocular implant 1300 include a first ventral loop 1364A, a second ventral loop 1364B, and a third ventral loop 1364C. Each ventral loop 1364 has first end and a second end that are both affixed to second side 1324 of spine portion 1302. Openings 1398 are disposed between the ventral loops 1364 and spine 1302. In the exemplary embodiment of FIG. 13, the loops are arranged so that no two loops cross each other.

Ocular implant 1300 defines a channel 1394 that opens into a channel opening 1396. The channel extends along the length of spine 1302. The channel opening is disposed opposite spine 1302 such that the channel opens away from spine 1302. With particular reference to FIG. 19B, it will be appreciated that the channel and the channel opening extending together between first dorsal loop 1362A and first ventral loop 1364A. The channel and the channel opening also extend between second dorsal loop 1362B and second ventral loop 1364B. The channel and the channel opening can also been seen extending together between third dorsal loop 1362C and third ventral loop 1364C in FIG. 19B.

Figure 20:
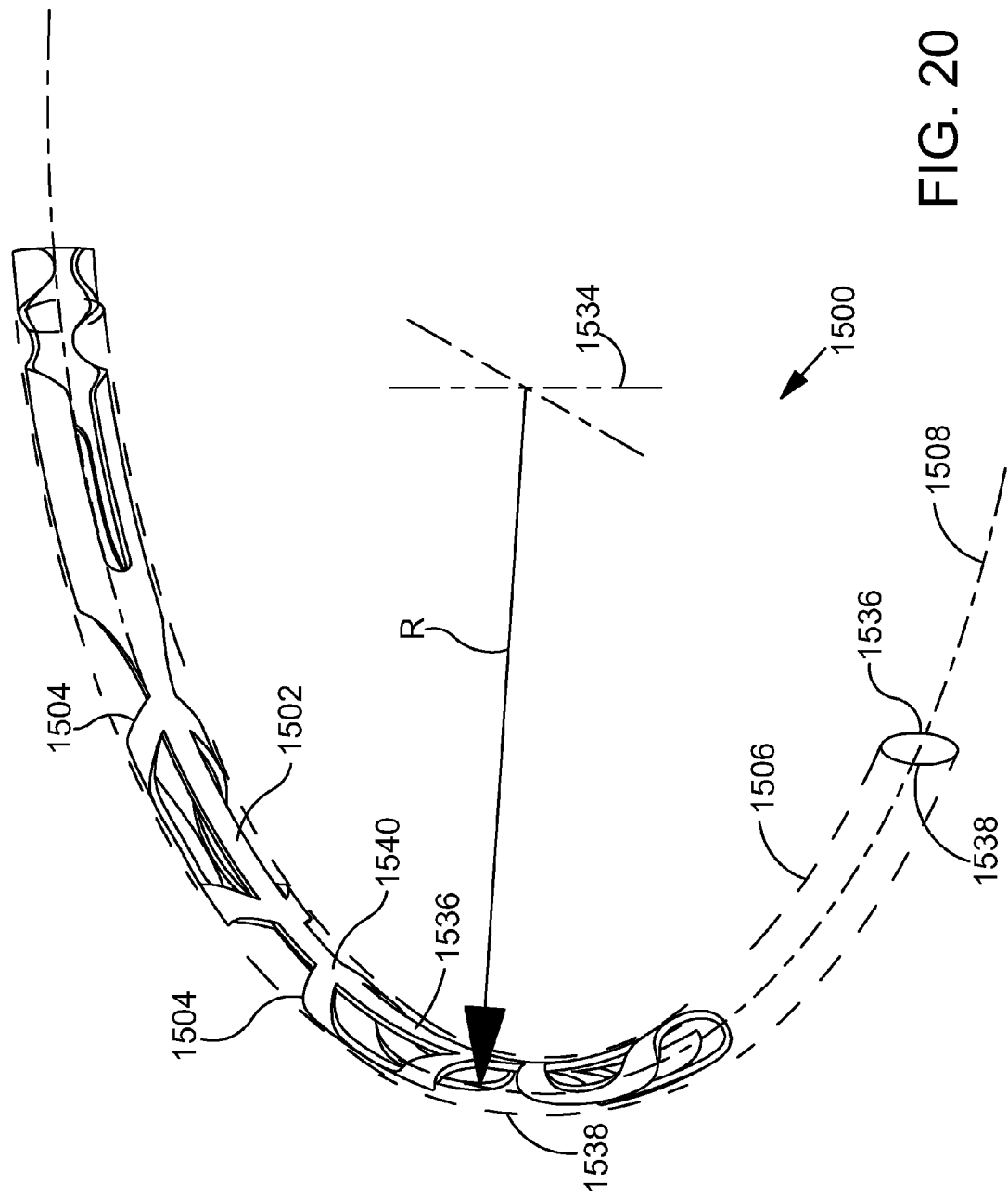
FIG. 20 is a perspective view of the ocular implant shown in the previous embodiment.

FIG. 20 is a perspective view of ocular implant 1500 shown in the previous embodiment. A radius R of longitudinal central axis 1508 is illustrated with an arrow in FIG. 20. The arrow illustrating radius R can be seen extending between a first lateral central axis 1534 and longitudinal central axis 1508 in FIG. 20. It will be appreciated that that radius R may be constant or may vary along the length of longitudinal central axis 1508. Volume 1506 has an inner major side 1536 and an outer major side 1538. Relative to radius R, inner major side 1536 of volume 1506 is disposed on a radially inward side of longitudinal central axis 1508. Outer major side 1538 of volume 1506 is disposed on a radially outward side of longitudinal central axis 1508 relative to radius R. With reference to FIG. 20, it will be appreciated that inner major side 1536 is closer to the first lateral central axis 1534 than outer major side 1538.

Ocular implants in accordance with this detailed description may be delivered into Schlemm's canal of a patient's eye. The ocular implants may be configured to facilitate the flow of aqueous humor out of the anterior chamber when placed in Schlemm's canal. The ocular implants may also be configured to facilitate advancement into Schlemm's canal and to minimize any trauma incurred by eye tissues during the delivery procedure. The ocular implants may be designed to include various features that promote these aspects of performance. In some cases, however, features which improve one aspect of performance may have a detrimental impact on another aspect of performance. When this is the case, design tradeoffs may be made between competing performance considerations.

When placed in Schlemm's canal, ocular implant 1500 of FIG. 20 will tend to assume an orientation in which spine 1502 is offset from the outer major wall of Schlemm's canal and aligned with a central portion of the inner major side of Schlemm's canal. Spine 1502 of ocular implant 1500 is aligned with a central portion 1540 of inner major side 1536 of volume 1506. Spine 1502 is also disposed in a location offset from outer major side 1538 of volume 1506 in the embodiment of FIG. 20. Positioning the spine in a location offset from the outer major wall of Schlemm's canal may serve to minimize the likelihood that the ocular implant will obstruct collector channels. Aligning the spine of the ocular implant with a central portion of the inner major wall of Schlemm's canal may provide good support for the trabecular meshwork. Accordingly, it will be appreciated that the arrangement shown in FIG. 20 will facilitate the flow of aqueous humor out of the anterior chamber of the eye.

Figure 21:
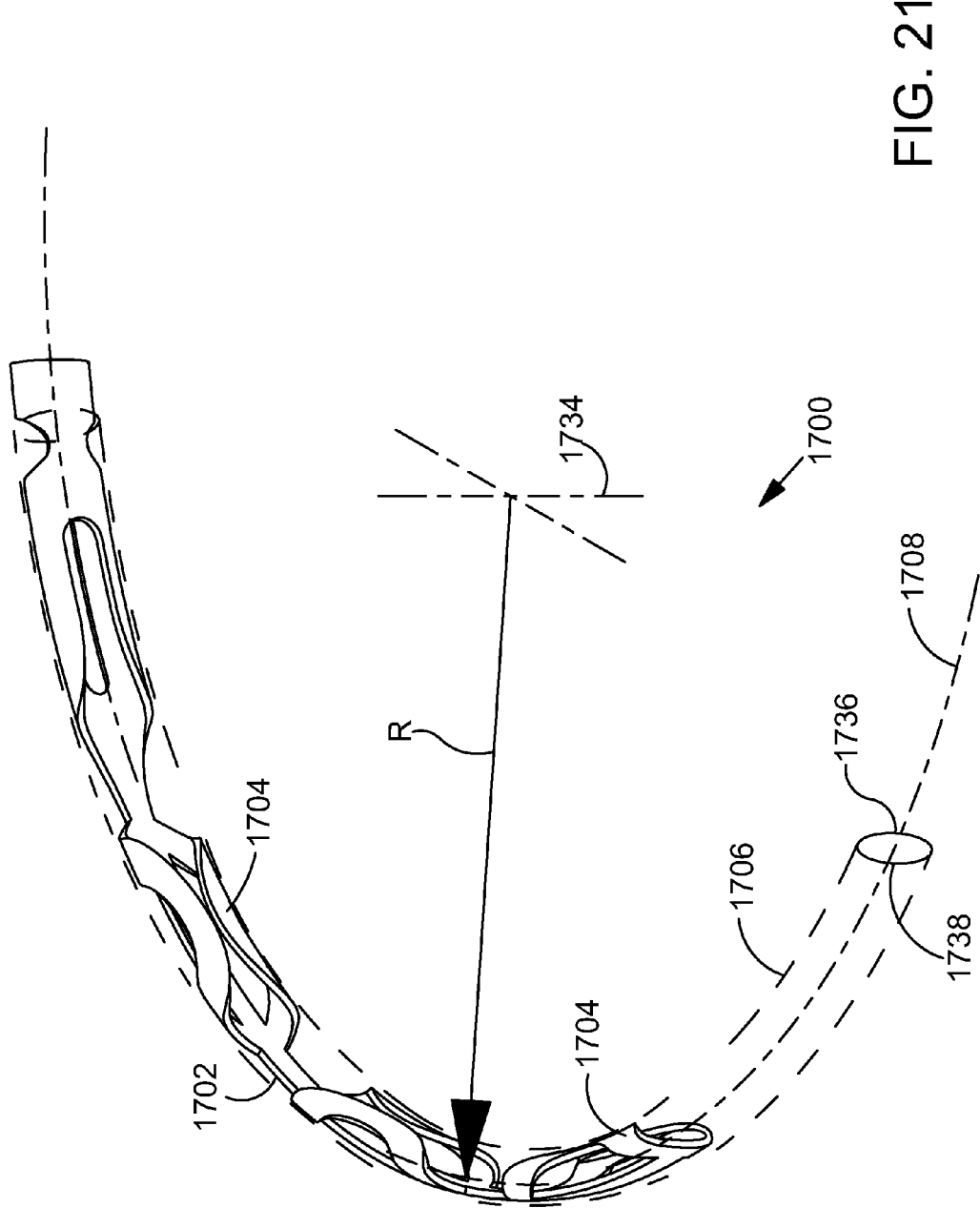
FIG. 21 is a perspective view illustrating an additional exemplary ocular implant in accordance with the detailed description.

FIG. 21 is a perspective view illustrating an additional exemplary ocular implant in accordance with the detailed description. Ocular implant 1700 of FIG. 21 comprises a spine 1702 from which a plurality of supports 1704 extend. With reference to FIG. 21, it will be appreciated that spine 1702 holds supports 1704 in a spaced apart relationship. Supports 1704 and spine 1702 define a volume 1706 that extends along a longitudinal central axis 1708 of ocular implant 1700.

In FIG. 21, spine 1702 and supports 1704 can be seen extending along longitudinal central axis 1708 of ocular implant 1700. In the embodiment of FIG. 21, longitudinal central axis 1708 follows a path that is generally curved. A radius R of longitudinal central axis 1708 is illustrated with an arrow in FIG. 21. Radius R may be constant or may vary along the length of longitudinal central axis 1708. In FIG. 21, the arrow illustrating radius R can be seen extending between a first lateral central axis 1734 and longitudinal central axis 1708. Volume 1706 has an inner major side 1736 and an outer major side 1738. Relative to radius R, inner major side 1736 of volume 1706 is disposed on a radially inward side of longitudinal central axis 1708. Outer major side 1738 of volume 1706 is disposed on a radially outward side of longitudinal central axis 1708 relative to radius R. With reference to FIG. 21, it will be appreciated that inner major side 1736 is closer to the first lateral central axis 1734 than outer major side 1738.

Ocular implants in accordance with this detailed description may be facilitate the flow of aqueous humor out of the anterior chamber, configured to facilitate delivery of the ocular implant into Schlemm's canal, and configured to minimize any trauma incurred by eye tissues during the delivery procedure. The ocular implants may be designed to include various features that promote these aspects of performance. In some cases, however, features which improve one aspect of performance may have a detrimental impact on another aspect of performance. When this is the case, design tradeoffs may be made between competing performance considerations.

With reference to FIG. 21, it will be appreciated that ocular implant 1700 includes a spine 1702 that is located on a longitudinally convex side of ocular implant 1700. An ocular implant including a spine located on a longitudinally convex side thereof may enable the spine 1702 to slide against the outer major wall of Schlemm's canal as ocular implant 1700 is advanced into Schlemm's canal. The spine may be supported by the scleral tissue of the eye that supports the outer major wall of Schlemm's canal. Accordingly, an ocular implant including a spine located on a longitudinally convex side thereof may reduce the trauma inflicted on the tissues of Schlemm's canal as ocular implant 1700 is advanced into Schlemm's canal during a delivery procedure.

In the embodiment of FIG. 21, spine 1702 of ocular implant 1700 is uninterrupted by any openings so that spine 1702 provide a continuous surface along its length. A spine having a continuous surface, uninterrupted by any openings, may reduce the trauma inflicted on the tissues of Schlemm's canal as ocular implant 1700 is advanced into Schlemm's canal during a delivery procedure.

Figure 22:
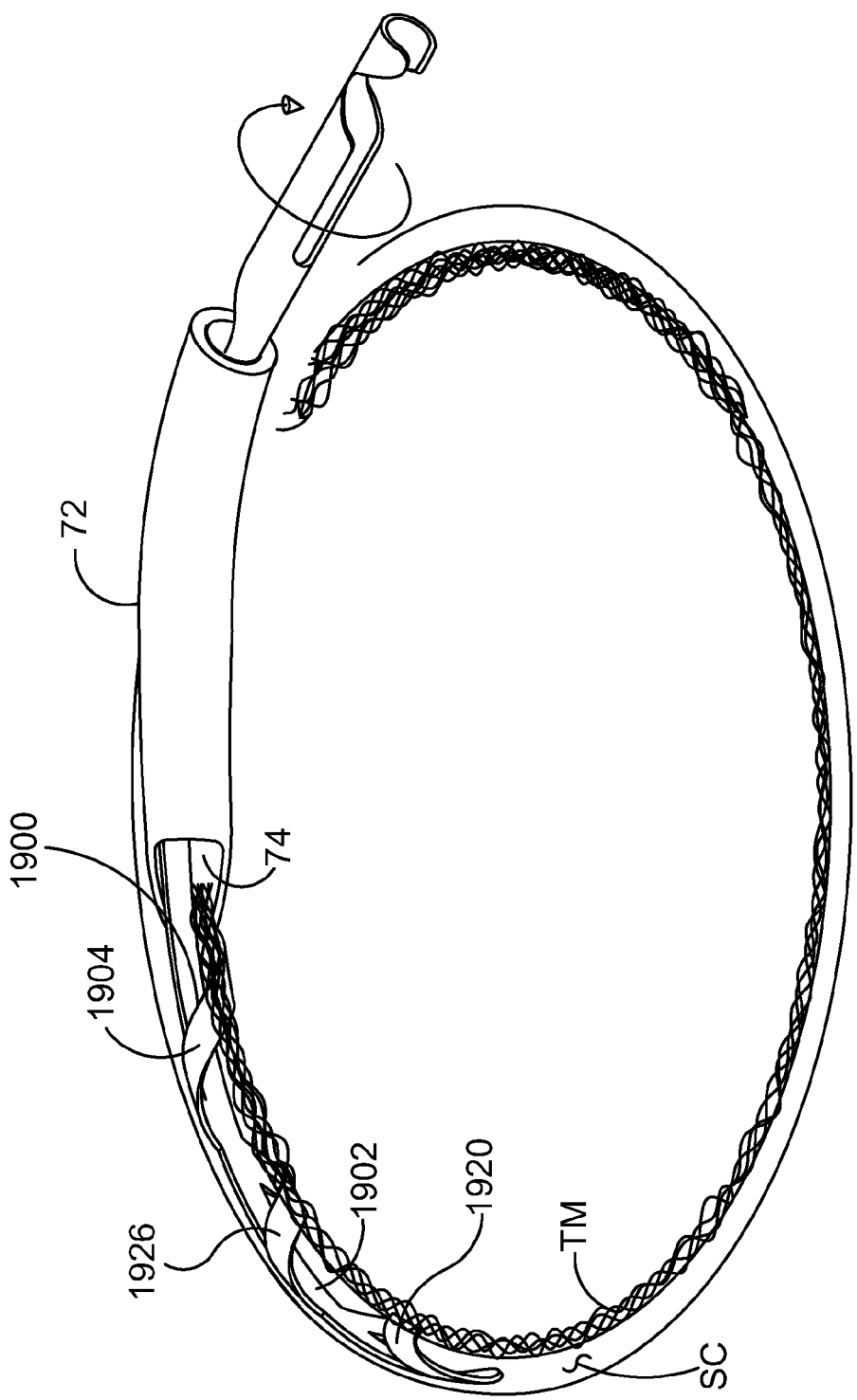
FIG. 22 is a stylized perspective view illustrating a method in accordance with the detailed description.

FIG. 22 is a stylized perspective view illustrating a method in accordance with this detailed description. Schlemm's canal SC and the trabecular meshwork TM of an eye are schematically illustrated in FIG. 22. In FIG. 22, an ocular implant 1900 is shown extending into Schlemm's canal SC. Ocular implant 1900 of FIG. 22, comprises a spine 1902 and a plurality of supports 1904 extending from spine 1902. In the embodiment of FIG. 22, each support 1904 comprises a loop 1920. In the exemplary embodiment of FIG. 22, loops 1920 are arranged to form a helix 1926.

A cannula 72 is shown in FIG. 22. Cannula 72 has a distal opening 74 that is disposed in fluid communication with Schlemm's canal SC. An exemplary method in accordance with this detailed description may include the step of advancing the distal end of a cannula through the cornea of a human eye so that a distal portion of the cannula is disposed in the anterior chamber of the eye. The cannula may then be used to access Schlemm's canal of the eye, for example, by piercing the wall of Schlemm's canal with the distal end of the cannula. A distal opening of the cannula may be placed in fluid communication with a lumen defined by Schlemm's canal. An ocular implant (such as, for example, ocular implant 1900 of FIG. 22) may be advanced out of the distal opening of the cannula and into Schlemm's canal. In the exemplary embodiment of FIG. 22, ocular implant 1900 is being rotated as it is advanced into Schlemm's canal SC. The rotation of ocular implant 1900 is illustrated with an arrow in FIG. 22. The helical shape of support portion 1904 may cause ocular implant 1900 to advance into Schlemm's canal as it is rotated. In this way, the helical shape of support portion 1904 may facilitate delivery of the ocular implant into Schlemm's canal and serve to minimize any trauma incurred by eye tissues during the delivery procedure.

While exemplary embodiments of the present invention have been shown and described, modifications may be made, and it is therefore intended in the appended claims to cover all such changes and modifications which fall within the true spirit and scope of the invention.

What is claimed is:

1. An ocular implant adapted to reside at least partially in a portion of Schlemm's canal of an eye, the implant comprising:
   a spine extending along a curved longitudinal axis of the implant on a convex side of the implant,
   a plurality of supports extending from the spine at a plurality of longitudinally spaced support locations, each support comprising a dorsal loop extending from a first side of the spine and a ventral loop extending from a second side of the spine opposite the first side, and
   an elongate opening extending along the longitudinal axis and bordered by the spine and the dorsal and ventral loops of the supports,
   the spine extending in a straight line continuously through the support locations,
   the spine and supports defining a volume having a maximum width perpendicular to the longitudinal axis between 0.005 inches and 0.04 inches,
   the ocular implant being configured to bend preferentially in a preferential bending plane.

2. The ocular implant of claim 1, wherein the longitudinal axis of the ocular implant is curved in the preferential bending plane.

3. The ocular implant of claim 1, wherein the volume defined by the ocular implant has a circular cross-section.

4. The ocular implant of claim 1, wherein the volume defined by the ocular implant has a non-circular cross-section.

5. The ocular implant of claim 4, wherein the spine is disposed on a longer side of the non-circular cross-section.

6. The ocular implant of claim 1 wherein:
   the spine has a width and a thickness; and
   an aspect ratio of the width to the thickness is such that the spine bends preferentially in the preferential bending plane.

7. The ocular implant of claim 6 wherein the aspect ratio of the width to the thickness is greater than one.

8. The ocular implant of claim 7 wherein the aspect ratio of the width to the thickness is about three.

9. The ocular implant of claim 1 wherein:
   the spine has a first lateral extent and a second lateral extent; and
   an aspect ratio of the first lateral extent to the second lateral extent is such that the spine bends preferentially in the preferential bending plane.

10. The ocular implant of claim 9 wherein the aspect ratio of the first lateral extent to the second lateral extent is greater than one.

11. The ocular implant of claim 10 wherein the aspect ratio of the first lateral extent to the second lateral extent is greater than three.

12. The ocular implant of claim 1, wherein the supports and spine define a lumen and a plurality of openings fluidly communicating with the lumen, the ocular implant being more than 50% open due to the openings defined by the supports and spine.

13. The ocular implant of claim 1, wherein the ocular implant is configured to reshape a trabecular meshwork of the eye when the ocular implant is placed within a portion of Schlemm's canal of the eye.

14. The ocular implant of claim 1, wherein the ocular implant is configured to reshape Schlemm's canal when the ocular implant is placed therein.

* * * * *